(12) United States Patent
Brain et al.

(10) Patent No.: US 7,045,533 B2
(45) Date of Patent: May 16, 2006

(54) NAPHTHALENE DERIVATIVES

(75) Inventors: Christopher T Brain, London (GB); Andrew J Culshaw, London (GB); Edward K Dziadulewicz, London (GB); Ulrich Schopfer, Lörrach (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/432,120

(22) PCT Filed: Nov. 22, 2001

(86) PCT No.: PCT/EP01/13605

§ 371 (c)(1),
(2), (4) Date: May 19, 2003

(87) PCT Pub. No.: WO02/42248

PCT Pub. Date: May 30, 2002

(65) Prior Publication Data

US 2004/0053890 A1 Mar. 18, 2004

(30) Foreign Application Priority Data

Nov. 24, 2000 (GB) .................................. 0028702.9

(51) Int. Cl.
*A61K 31/47* (2006.01)
*C07D 215/00* (2006.01)
*C07D 217/00* (2006.01)

(52) U.S. Cl. ...................... 514/311; 546/139; 546/153; 548/250; 548/251; 548/262.2

(58) Field of Classification Search ................ 546/139, 546/153; 548/262.2, 250, 251; 514/311
See application file for complete search history.

(56) References Cited

U.S. PATENT DOCUMENTS

| 1,874,581 A | 8/1932 | Neelmeier et al. | |
| 5,430,062 A | 7/1995 | Cushman et al. | |
| 5,679,866 A | 10/1997 | Curtze et al. | |
| 5,773,663 A | 6/1998 | Curtze et al. | |
| 5,866,722 A | 2/1999 | Curtze et al. | |
| 5,922,905 A * | 7/1999 | Curtze et al. | 562/474 |
| 5,939,429 A | 8/1999 | Sanyal et al. | |
| 6,090,850 A * | 7/2000 | Goodson et al. | 514/563 |
| 6,130,226 A * | 10/2000 | Muller et al. | 514/277 |
| 6,262,112 B1 | 7/2001 | Mittendorf et al. | |
| 6,348,631 B1 * | 2/2002 | Desmurs et al. | 568/319 |

FOREIGN PATENT DOCUMENTS

| DE | 10 16 717 B | 10/1957 |
| EP | 727 141 A2 | 8/1996 |
| GB | 1200273 | 7/1970 |
| WO | WO 93/23357 | 11/1993 |
| WO | WO 98/37061 | 8/1998 |
| WO | WO 99/24404 | 5/1999 |

OTHER PUBLICATIONS

Goodson et al (1997): STN International CAplus database, Columbus (Ohio), Accession No.: 1997:500185.*
Kita Y. et al., Journal of Organic Chemistry, "Novel and direct nucleophilic sulphenylation and thiocyanation of phenol ethers using a hypervalent iodine (III) reagent", vol. 60, No. 22, pp. 7144-7148 (1995) *.
Zieger H.E. et al., Journal of Organic Chemistry, "2-Chloro-3-dimethylamino-6-phenylsulphonyl-phenyllithium", vol. 27, No. 9, pp. 3270-3273 (1962) *.
Schroeter G., Berichte Der Deutschen Chemischen Gesellschaft, "Uber Acyierung von Anilin-sulfosauren", vol. 39, pp. 1559-1570 (1906) *.
Huisgen R. et al., Tetrahedron Letters, "Zur Thermolyse des 2-Azido-4, 6-dimethyl-pyrimidins; Reaktionen des Azens", No. 30, pp. 2595-2598 (1969) *.
Kurzer F., Journal of the Chemical Society, "The conversion of arylamines into symmetrical diarylureas. The melting points of certain substituted ureas", pp. 2292-2295 (1949) *.
Neidlein R. et al., Liebigs Annalen Der Chemie, "Heterocyclische 12-pi- und 14-pi-systeme, 34 Untersuchungen zum Reaktionsverhalten von 2-Phenyl-5H-naphtho[1,8-bc] furan-2-on (Oxapseudophenalenon)", No. 7, pp. 959-964 (1979) *.
Nakayma T. et al., Chemical and Pharmaceutical Bulletin, "Synthesis and structure-activity study of protease inhibitors. II. Amino- and guanidino-substituted naphthoates and tetrahydronaphthoates", vol. 32, No. 10, pp. 3968-3980 (1984) *.

(Continued)

Primary Examiner—Golam M. M. Shameem
(74) Attorney, Agent, or Firm—Peter J. Waibel; E. Jay Wilusz

(57) ABSTRACT

The present invention relates to novel naphthalene derivatives of formula (I), wherein $R^1$, $R^2$, $R^3$ and X are as defined in the description, and preparation thereof. The compounds of formula (I) are useful as pharmaceuticals.

4 Claims, No Drawings

OTHER PUBLICATIONS

Doak G.O. et al., Journal of the American Chemical Society, "Arsene oxides of naphthalene and biphenyl", vol. 64, No. 5, pp. 1064-1066 (1942) *.

Denny W.A. et al., Journal of Medicinal Chemistry, "Potential antitumour agents. 29. Quantitative structure-activity relationships for the antileukaemic bisquaternary ammonium heterocycles", vol. 22, No. 2, pp. 134-150 (1979)*.

Michne W.F. et al., Journal of Medicinal Chemistry, "Novel inhibitors of potassium ion channels on human T lymphocytes", vol. 11, No. 38, pp. 1877-1883 (1995) *.

Gangjee A. et al., Journal of Medicinal Chemistry, "2,4-Diamino-5-deaza-6-Substituted Pyrido[2,3-d]pyrimidine Antifolates as Potent and Selective Nonclassical Inhibitors of Dihydrofolate Reductases", vol. 39, No. 7, pp. 1438-1446 (1996).

Gangjee A. et al., Journal of Medicinal Chemistry, "6-Substituted 2,4-Diamino-5-methylpyrido[2,3-d]pyrimidines as Inhibitors of Dihydrofolate Reductases from Pneumocystis carinii and Toxoplasma gondii and as Antitumour Agents", vol. 38, No. 10, pp. 1778-1785 (1995) *.

Taniyama D. et al., Tetrahedron Letters, "A facile and efficient asymmetric synthesis of (+)-salsolidine", vol. 41, No. 29, pp. 5533-5536 (2000) *.

Noelting E. et al., Berichte Der Deutschen Chemischen Gesellschaft, "Ueber Farbstoffe der Naphtyl-diphenyl-methan-Dinaphtyl-phenyl-methan- und Trinaphtyl-methan-Reihen", vol. 37, pp. 1899-1920 (1904) *.

Chauzov V.A., Journal of General Chemistry of the USSR, "Stereospecific transition from phenyl(1-naphthyl)phosphinothioic acid to S-ethyl phenyl(1-naphthyl)phosphinothioate, methyl phenyl(1-naphthyl)phosphinate, and N,N-diethyl-P-phenyl-P-(1-naphthyl)phosphinic amide", vol. 51, No. 8, p. 1650 (1981) *.

Grellmann K.H. et al., Journal of the American Chemical Society, "Reactivity and decay pathways of photoexcited anilinonaphthalenes", vol. 104, No. 23, pp. 6267-6272 (1982) *.

Cavallito C.J. et al., Journal of Medicinal Chemistry, "Choline acetyltransferase inhibitors, Styrylpyridine analogues with nitrogen-atom modifications", vol. 14, No. 2, pp. 130-133 (1971) *.

Al-Khamees H. A. et al., Eur. J. Med. Chem. "Synthesis and pharmacological screening of a new series of 3-(4-antipyryl)-2-arylthiazolidin-4-ones", vol. 25, pp. 103-106 (1990).

Chemical Abstracts, vol. 109:129009h (1988).

Meyers A.I. et al., J.Org.Chem., "An Asymmetric Synthesis of (+)-Morphinans in High Enantiomeric Purity", vol. 51, pp. 872-875 (1986).

Schreiber K.C. et al., J.Org.Chem., "4-methoxy-1-naphthalenemethanol", vol. 21, pp. 1310-1311 (1956).

R. Quelet et al., Compt. Rend. vol. 246, pp. 1566-1568 (1958).

Chemical Abstracts, vol. 52:13693h.

Broquet-Borcel C. et al., Compt. Rend. vol. 249, pp. 1761-1763 (1959).

Chemical Abstracts, vol. 54:9855c.

Greener M., Pharma Market Letter "Ensuring cannabinoids' potential does not go to pot", pp. 24-25 (2000).

Chemical Abstracts, vol. 54:1435e (1957).

Chemical Abstracts, vol. 71:81297t (1969).

Chemical Abstracts, vol. 91:211166a (1979).

* cited by examiner

NAPHTHALENE DERIVATIVES

The present invention relates to novel naphthalene derivatives, to processes for their production, their use as pharmaceuticals and to pharmaceutical compositions comprising them.

More particularly the present invention provides in a first aspect, a compound of formula I

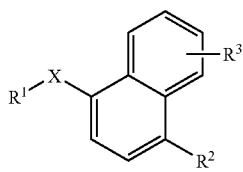

(I)

wherein
X is —S—, —S(O)—, —S(O)$_2$—, —S(O)$_2$NH—, —P(O)(OCH$_3$)—, —P(O)(OH)—, —NH—, —N(CH$_3$)—, —NHC(O)NH—, —C(O)—, —C(O)O—, —NHC(O)—, —CH(OH)—, —CH=N—, —CH=CH—, —CH$_2$NH— or —C(=NH)—;
$R^1$ is aryl or heteroaryl;
$R^2$ is hydrogen, $OR^4$ or $NR^5R^6$;
  $R^4$ is $C_1$–$C_8$alkyl or $C_2$–$C_8$alkenyl;
  $R^5$ and $R^6$ independently are hydrogen, $C_1$–$C_8$alkyl or C(O)$C_1$–$C_8$alkyl; and
$R^3$ is hydrogen, cyano, heteroaryl, heterocycloalkyl, C(O)$R^7$, $OR^8$ or $NR^9R^{10}$;
  $R^7$ is OH, $C_1$–$C_4$alkoxy, NH$_2$, NHCH$_2$C(O)OH or aryl;
  $R^8$ is hydrogen, $C_1$–$C_8$alkyl, C(O)$C_1$–$C_4$alkyl or C(O)-aryl; and
  $R^9$ and $R^{10}$ independently are hydrogen, $C_1$–$C_8$alkyl or $C_2$–$C_4$alkenyl;

with the proviso that when X is —C(O)— and $R^2$ and $R^3$ are hydrogen or $R^2$ is H and $R^3$ is 4-methoxy, $R^1$ is neither 1-naphthyl nor 4-methoxy-1-naphthyl;
in free base or acid addition salt form.

Aryl or heteroaryl is to be understood to include a six membered ring or a bicycle consisting of two condensed six-membered rings or one six-membered and one five-membered ring, wherein one or more C atoms may be replaced, independently of one another, by an atom selected from the group consisting of oxygen, nitrogen and sulfur. Examples include $C_6$–$C_{10}$aryl, $C_1$–$C_9$heteroaryl, and $C_6$aryl condensed to a five or six membered aliphatic or heteroaliphatic ring, e.g. naphthyl, 1,2,3,4-tetrahydronaphthalenyl, phenyl, indolyl, quinolinyl, isoqulnolinyl, 1,2,3,4-tetrahydroquinolinyl, benzothiazolyl, imidazolyl, benzimidazolyl, benzoxadiazolyl, benzotriazolyl, indanyl, oxadiazolyl, pyrazolyl, triazolyl and tetrazolyl.

Examples for heterocycloalkyl include piperidinyl, piperazinyl and morpholinyl.

It will be understood that the above defined compounds may bear substituents within their structure, e.g. one or more substituents selected from OH; nitro; halogen; cyano; COOH; C(O)NH$_2$; C(O)NHNHC(O)CH$_3$; C(NH$_2$)=NOH; $C_1$–$C_4$alkyl; S—$C_1$–$C_4$alkyl; $C_1$–$C_8$alkoxy; $C_5$–$C_{10}$aryl such as phenyl; $C_1$–$C_4$-heteroaryl such as oxadiazolyl; $C_1$–$C_5$-N-heterocycloalkyl such as morpholinyl or piperidinyl; C(O)O—$C_1$–$C_4$alkyl or $NR^{11}R^{12}$ wherein $R^{11}$ and $R^{12}$ independently are hydrogen, $C_1$–$C_4$alkyl, C(O)NHOC$_1$–$C_4$alkyl, C(O)$C_1$–$C_4$alkyl or SO$_2$—$C_1$–$C_4$alkyl; which substituents again may be substituted by a substituent selected from OH; nitro; NH$_2$; $C_1$–$C_4$alkyl; $C_1$–$C_4$alkoxy; $C_1$–$C_4$alkoxy substituted by OH; $C_3$–$C_6$cycloalkyl; N—($C_1$–$C_4$alkyl)$_2$; phenyl; or morpholinyl.

For example, in the meaning of $R^1$ aryl or heteroaryl may be unsubstituted or substituted by one or more substituents selected from OH; COOH; C(O)NH$_2$; nitro; halogen; cyano; C(NH$_2$)=NOH; $C_1$–$C_4$—N-heteroaryl; $C_1$–$C_5$—N-heterocycloalkyl; $C_1$–$C_4$alkyl; S—$C_1$–$C_4$alkyl; $C_1$–$C_8$alkoxy and $NR^{11}R^{12}$ wherein $R^{11}$ and $R^{12}$ independently are hydrogen, $C_1$–$C_4$alkyl, C(O)NHOC$_1$–$C_4$alkyl, C(O)$C_1$–$C_4$alkyl or SO$_2$–$C_1$–$C_4$alkyl; wherein $C_1$–$C_4$alkyl, $C_1$–$C_8$alkoxy and $C_1$–$C_5$—N-heterocycloalkyl again may be unsubstituted or substituted by OH; $C_1$–$C_4$alkyl; $C_1$–$C_4$alkoxy;, $C_1$–$C_4$alkoxy substituted by OH; $C_3$–$C_6$cycloalkyl; N—($C_1$–$C_4$alkyl)$_2$; phenyl; or morpholinyl;

in the meaning of $R^3$ oxadiazolyl, piperazinyl or tetrazolyl may be substituted by methyl;

in the meaning of $R^4$ $C_1$–$C_8$alkyl may be unsubstituted or substituted by OH, C(O)O—$C_1$–$C_4$alkyl, morpholinyl, piperidinyl, phenyl or oxadiazolyl; wherein phenyl and oxadiazolyl again may be unsubstituted or substituted by $C_1$–$C_4$alkyl, $C_1$–$C_4$alkoxy, nitro, NH$_2$ or N($C_1$–$C_4$alkyl)$_2$;

in the meaning of $R^5$ or $R^6$ $C_1$–$C_4$alkyl may be unsubstituted or substituted by morpholinyl;

in the meaning of $R^8$ $C_1$–$C_4$alkyl may be unsubstituted or substituted by C(O)OH, C(O)OCH$_3$, C(O)NHNHC(O)CH$_3$ or oxadiazole substituted by $C_1$–$C_4$alkyl.

Compounds of the invention exist in free or salt, e.g. acid addition salt form. The invention is to be understood as including the compounds of formula I in free as well as in salt form, e.g. as trifluoroacetate or hydrochloride salt. Suitable pharmaceutically acceptable acid addition salts for pharmaceutical use in accordance with the invention include in particular the hydrochloride salt.

In formula I the following significances are preferred independently, collectively or in any combination or sub-combination:

(a) X is —S—, —S(O)—, S(O)$_2$—, —S(O)$_2$NH—, —P(O)(OCH$_3$)—, —P(O)(OH)—, —NH—, —N(CH$_3$)—, —NHC(O)NH—, —NHC(O)—, —C(O)—, —C(O)O—, —CH(OH)—, —CH=N—, —CH=CH—, —CH$_2$NH— or —C(=NH)—; particularly —NH—, —C(O)—, —C(O)O— or —CH$_2$NH—, more particularly —C(O)— or —C(O)O—;

(b) $R^1$ is phenyl, 4-methoxyphenyl, 2-hydroxy-3-methoxyphenyl, 2,3-dimethoxyphenyl, 3,4-dimethoxyphenyl, 4-[2-(morpholin-4-yl)ethoxy]phenyl, 4-[3-(hydroxy)propoxy]phenyl, 4-butoxyphenyl, 3-(NHC(O)NHOCH$_3$)-4-pentoxyphenyl, 4-thiomethylphenyl, 4-acetamido-phenyl, naphthyl, 4-carboxynaphthyl, 4-aminocarbonylnaphthyl, 4-hydroxynaphthyl, 4-(C(NH$_2$)=NOH)-naphthyl, 4-fluoro-naphth-1-yl, 4-cyanonaphthyl, 3-nitro-naphth-1-yl, 4-nitro-naphth-1-yl, 3-amino-naphth-1-yl, 4-amino-naphth-1-yl, 4-dimethylamino-naphth-1-yl, 4-methoxy-naphth-1-yl, 4-[4-(hydroxy)butoxy]naphthyl, 4-pentoxy-naphthyl, 4-[2-(morpholin-4-yl)ethoxy]naphthyl, 3-(dimethylamino)naphthyl, 3-methylsulfonamido-naphthyl, 4-methylsulfonamido-naphthyl, 4-methyl-sulfonamide-naphthyl, 4-(1,2,4-triazol-1-yl)-naphth-1-yl, 4-(1H-tetrazol-5-yl)-naphthyl, 4-(pyrazol-1-yl)-naphthyl, 4-(imidazol-1-yl)-naphthyl, 1,2,3,4-tetrahydronaphthalen-5-yl, indan-4-yl, indol-7-yl, quinolin-8-yl, quinolin-4-yl, quinolin-3-yl, quinolin-5-yl, isoquinolin-5-yl, isoquinolin-1-yl, 1,2,3,4-tetrahydroquinolin-1-yl, 1,2,3,4-tetrahydroquinolin-8-yl, 6-methoxy-1,2,3,4-tetrahydroquinolin-1-yl, 5-hydroxy-1,2,3,4-tetrahydroquinolin-1-yl, 7-pentoxy-benzotriazol-4-yl, 5,7-dimethyl-2,1,3-benzothiadiazol-4-yl, 5-chloro-2,1,3-benzothiadiazol-4-yl, 2,1,3-benzothladiazol-4-yl, 2,1,3- benzoxadiazol-4-yl, 7-pentoxy-2,1,3-benzoxadiazol-4-yl, 2-oxo-7-pentoxy-1,3-dihydro-benzimidazol-4-yl, 2-(NHCH₂phenyl)-7-pentoxy-benzimidazol-4-yl, 2-(NHCH₂cyclohexyl)-7-pentoxy-benzimidazol-4-yl, 2-(NH(CH₂)₃N(CH₂CH₃)₂)-7-pentoxy-benzimidazol-4-yl, 2-(NH(CH₂)₃CH₃)-7-pentoxy-benzimidazol-4-yl, 2-(4-methylplperazin-1-yl)-7-pentoxy-benzimidazol-4-yl, 2-(NH(CH₂)₂OH)-7-pentoxy-benzimidazol-4-yl, 2-(NH(CH₂)₂O(CH₂)₂OH)-7-pentoxy-benzimidazol-4-yl, 2-methyl-7-pentoxy-benzimidazol-4-yl, 7-pentoxy-benzimidazol-4-yl; particularly naphthyl, 4-hydroxynaphthyl, 4fluoro-naphth-1yl, 4-cyanonaphth-1-yl, 4-nitro-naphth-1-yl, 4-dimethylamino-naphth-1-yl, 4-methoxy-naphth-1-yl, 4-[4-(hydroxy)butoxy]naphthyl, 4-(1,2,4-triazol-1-yl)-naphth-1-yl, 4-(pyrazol-1-yl)-naphthyl, 4-(imidazol-1-yl)-naphthyl, 1,2,3,4-tetrahydronaphthalen-5-yl, indan-4-yl, quinolinyl, quinolin-8-yl, quinolin-4-yl, isoquinolin-5-yl, 7-pentoxy-benzotriazol-4-yl, 5-chloro-2,1,3-benzothiadiazol-4-yl, 2-(NHCH₂phenyl)-7-pentoxy-benzimidazol-4-yl, 2-(NH(CH₂)₃CH₃)-7-pentoxy-benzimidazol-4-yl or 7-pentoxybenzimidazol-4-yl, more particularly naphthyl, 4-fluoro-naphth-1-yl, 4-cyanonaphth-1-yl, 4-cyanonaphth-1-yl, 4-dimethylamino-naphth-1-yl, 4-(1,2,4-triazol-1-yl)-naphth-1-yl, 4-(imidazol-1-yl)-naphthyl, 1,2,3,4-tetrahydronaphthalen-5-yl, indan-4-yl, quinolin-8-yl, isoquinolin-5-yl or 5-chloro-2,1,3-benzothiadiazol-4-yl;

(c) R² is hydrogen, —O—(CH₂)₂CH₃, —O—(CH₂)₃CH₃, —O—(CH₂)₄CH₃, —O—(CH₂)₅CH₃, —O—(CH₂)₆CH₃, —O—(CH₂)₃CH(CH₃)₂, 2-(morpholin-4-yl)-ethoxy, 2-(piperidin-1-yl)-ethoxy, 2-(4-methoxyphenyl)-ethoxy, 2-(phenyl)-ethoxy, 2-(4-nitrophenyl)-ethoxy, 2-(4-dimethylaminophenyl)-ethoxy, 2-(4-aminophenyl)-ethoxy, 2-(2-nitrophenyl)-ethoxy, 2-(2-aminophenyl)-ethoxy, 2-(2-dimethylaminophenyl)-ethoxy, 3-(morpholin-4-yl)-propyloxy, 3-(piperidin-1-yl)-propyloxy, —O—(CH₂)₃C(O)OCH₂CH₃, —O—(CH₂)₄C(O)OCH₂CH₃, —O—(CH₂)₂OCH₂CH₃, —O—CH₂C(O)OCH₃, —O—CH₂-(2-methyl)-oxadiazol-5-yl, —O—CH₂-(2-ethyl)-oxadiazol-5-yl, —O—CH₂-(2-propyl)-oxadiazol-5-yl, O—CH₂CH═CHCH₂CH₃ (Z) and (E), —O—(CH₂)₃OH, —O—(CH₂)₄OH, —O—(CH₂)₅OH, —N—[2-(morpholin-4-yl)-ethyl]-N—(CH₂)₃CH₃, —NH—(CH₂)₃CH₃, —NH—(CH₂)₄CH₃, —NHC(O)(CH₂)₃CH₃, —N(CH₃)(CH₂)₃CH₃ or —N(CH₃)(CH₂)₄CH₃; particularly hydrogen, —O—(CH₂)₂CH₃, —O—(CH₂)₃CH₃, —O—(CH₂)₄CH₃, —O—(CH₂)₅CH₃, —O—(CH₂)₃CH(CH₃)₂, 2-(morpholin-4-yl)-ethoxy, O—CH₂CH═CHCH₂CH₃ (Z) and (E), —NH—(CH₂)₃CH₃, —NH—(CH₃)(CH₂)₃CH₃ or —N(CH₃)(CH₂)₄CH₃; more particularly —O—(CH₂)₃CH₃, —O—(CH₂)₄CH₃, —O—(CH₂)₃CH(CH₃)₂, —O—CH₂CH═CHCH₂CH₃ (Z) and (E), —NH—(CH₂)₃CH₃, —NH—(CH₂)₄CH₃, —N(CH₃)(CH₂)₃CH₃ or —N(CH₃)(CH₂)₄CH₃;

(d) R³ is hydrogen, 7-OH, 8-OH, 7-OCH₃, 7-OCH₂C(O)OH, 7-OCH₂C(O)OCH₃, 7-OCH₂C(O)NHNHC(O)CH₃, 7-[—O—CH₂-(2-methyl)-1,3,4-oxadiazol-5-yl], 7-OC(O)CH₃, 7-OC(O)-naphthyl, 3-C(O)OH, 7-C(O)OH, 3-C(O)OCH₃, 7-C(O)NH₂, 8-OC(O)-naphthyl, 3-C(O)NHCH₂C(O)OH, 7-cyano, 6-NH₂, 7-NH₂, 6-N(CH₃)₂, 7-N(CH₃)₂, 6-NHCH₂CH═CH₂, 6-N(CH₂CH═CH₂)₂, 7-(piperidin-1-yl), 7-(4-methylpiperazin-1-yl), 7-(1H-tetrazol-5-yl), 7-(1-methyl)tetrazol-5-yl), 7-(2-methyl)tetrazol-5-yl) or 7-(2-methyl)-1,3,4-oxadiazol-5-yl; particularly hydrogen, 7-OH, 8-OH, 7-OC(O)CH₃ or 6-NHCH₂CH═CH₂; more particularly hydrogen, 7-OH or 7-OC(O)CH₃.

In addition to the foregoing the present invention also provides a process for the production of a compound of formula I which process comprises coupling an aryl or heteroaryl moiety to a suitably substituted naphthalene if necessary followed by further derivatisation according to methods known to the skilled artisan.

More particularly the invention provides a process for the production of a compound of formula I, comprising the steps of (a) reacting a compound of formula II $$R^1-R^{13} \quad (II)$$

wherein R¹ is as defined above and R¹³ is —OH, —SH, —I, —Cl, 1,8-bis(dimethylamino)naphthyl-, —COOH, —NH₂, —H, -carbontrile, —O-trifluoromethansulfonyl, or —C(O)Cl, with a compound of formula III

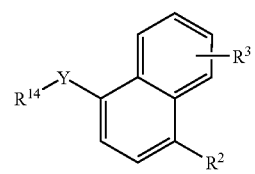

wherein R² and R³ are as defined above, Y is —O—, —S(O)₂O—, —P(O)(OCH₃)—, a single bond, —C(O)O—, —C(O)— or —B(OH)₂—, and R¹⁴ is e.g. hydrogen, —I, —Cl, thus obtaining a compound of formula Ia

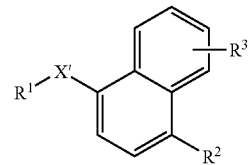

wherein R¹, R² and R³ are as defined above, and X' is CO—, —S—, —P(O)(OCH₃)—, —NH—, —S(O)₂NH—, —C(O)O—, —CH═N—, —CH(OH)—, —NHC(O)NH—, —C(═NH)—, or (when linked to a nitrogen atom of R¹) —S(O)₂—; or (b) converting a compound of formula Ia into a compound of formula Ib

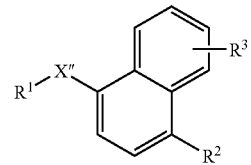

wherein R¹, R² and R³ are as defined above, and X" is —SO—, —S(O)₂— (obtainable via process (b) when binding partner at R¹═C), —N(CH₃)—, —P(O)OH—, —CH₂NH—, —CH═CH— or (when linked to a carbon atom of R¹) —S(O)₂— and recovering the so obtained compound of formula Ia and formula Ib in free form or in form of a salt.

Process (a) may be performed according to conventional procedures, e.g. as described in example 1 to 14.

According to process (b),
(i) for the production of a compound of formula Ib wherein X" is SO— or —S(O)$_2$—, a compound of formula Ia wherein X' is —S— and m-chloroperbenzoic acid can be used, e.g. as described in example 2;
(ii) for the production of a compound of formula Ib wherein X" is —P(O)OH—, a compound of formula Ia wherein X' is —P(O)(OCH$_3$)— and trimethylsilyl iodide can be used, e.g. as described in example 3;
(iii) for the production of a compound of formula Ib wherein X" is —N(CH$_3$)—, a compound of formula Ia wherein X' is —NH— and methyl iodide can be used, e.g. as described in example 4;
(iv) for the production of a compound of formula Ib wherein X" is —CH$_2$NH—, a compound of formula Ia wherein X' is —CH=N— and BH$_3$-pyridine can be used, e.g. as described in example 8.

Working up the reaction mixtures and purification of the compounds thus obtained may be carried out in accordance to known procedures.

Acid addition salts may be produced from the free bases in known manner, and vice-versa. Suitable acid addition salts for use in accordance with the present invention include for example the hydrochloride.

The starting compounds of formula II and III may be produced e.g. as described in example 2, 3, 5, 6, 12, 13 and 14; or are known or may be produced in analogous manner to known procedures.

The compounds of the invention and their pharmaceutically acceptable acid addition salts, hereinafter referred to as agents of the invention, exhibit valuable pharmacological properties when tested in vitro and in animals, and are therefore useful as pharmaceuticals.

In particular the agents of the invention exhibit cannabinoid (CB) receptor binding activity. More particularly the agents of the invention are active at the human CB$_1$ receptor. Cannabinoid receptor interaction of the agents of the invention may be demonstrated by their ability to displace e.g. [$^3$H]CP55940 from human cannabinoid receptors expressed In, e.g. pEAK cells, e.g. as demonstrated in accordance with the following test method.

Test I: CB1 Receptor Binding Assay

The assay mixture comprises 75 µl of membrane suspension [membranes from pEAK cells transfected with human CB1 receptors from Receptor Biology, Beltsville, Md.; 133 µg/ml in assay buffer (50 mM Tris-HCl, 2.5 mM EDTA, 5 mM MgCl$_2$ 5 mg/ml BSA, pH7.4), approx, 10 µg/well)], 25 µl WGA-YS beads [Yttrium silicate beads coated with wheat germ agglutinin, Amersham (40 mg/ml, 1 mg/well)], 50 µl test compound in 4% DMSO and 50 µl radioligand {[$^3$H]CP55940 (180 Ci/mmol), New England Nuclear, final concentration 0.125 nM, in assay buffer}. All components are mixed, shaken at room temperature for 2 hours, then counted on a Topcount. Non-saturable binding is measured in the presence of 10 µM (R)-(+)-[2,3-dihydro-5-methyl-3-[(4-morpholinyl)methyl]pyrrolo[1,2,3-de]-1,4-benzoxazin-6-yl](1-naphthalenyl)methanone (Tocris).

K$_i$ values are in the range of 1 nM to 100 µM, preferentially from 10 nM to 2 µM for the agents of the invention. The IC$_{50}$ values are calculated in ORIGIN using a logistic fit. K$_i$ values are calculated from the IC$_{50}$ values using the Cheng-Prussoff equation (K$_i$=IC$_{50}$/(1+([L]K$_d$)) where [L] is the ligand concentration.

The agents of the invention are particularly useful in the treatment or prevention of chronic pain, especially inflammatory, e.g. chronic inflammatory pain, inflammatory diseases for example inflammatory airways disease, e.g. COPD, or in asthma, rhinitis, inflammatory bowel disease, cystitis, e.g. interstitial cystitis, pancreatitis, uveitis, inflammatory skin disorders and rheumatoid arthritis.

Activity specifically as analgesic agents may be confirmed in accordance with standard test methods, e.g. as described in the following test Test II: Neuropathic Pain Model Hyperalgesia is examined in the model of neuropathic pain Induced by partial ligation of the sciatic nerve as described by Seltzer et al. (1990). Briefly, Wistar rats (120–140 g) are anaesthetised, the left sciatic nerve exposed at mid-thigh level through a small incision and ⅓ to ½ of the nerve thickness tightly ligated within a 7.0 silk suture. The wound is closed with a single muscle suture and skin clips and dusted with Aureomycin antibiotic powder. The animals are allowed to recover and used 12–15 days following surgery.

Mechanical hyperalgesia is assessed by measuring paw withdrawal thresholds to an increasing pressure stimulus placed onto the dorsal surface of the paw using an analgesymeter (Ugo-Basile, Milan) with a cut-off of 250 g. Withdrawal thresholds are measured on both the ipsilateral (ligated) and contralateral (unligated) paw prior to (predose) and then up to 6 h following drug or vehicle administration. Data are expressed as withdrawal threshold (g) and percentage reversal of hyperalgesia calculated according to the following formula:

$$\% \text{ reversal} = \frac{\text{ipsilateral threshold postdose} - \text{ipsilateral threshold predose}}{\text{contralateral threshold predose} - \text{ipsilateral threshold predose}} \times 100$$

Potency is expressed as D$_{50}$ value, i.e. the dose of compound necessary to produce 50% reversal of hyperalgesia.

D$_{50}$ values are in the range of 0.1 mg/kg to 100 mg/kg for the agents of the invention.

The agents of the invention are thus useful as cannabinoid receptor agonists, e.g. for the treatment of pain of various genesis or aetiology and as anti-inflammatory and/or anti-oedemic agents for the treatment of inflammatory reactions, diseases or conditions, as well as for the treatment of allergic responses. Having regard to their analgesic/anti-inflammatory profile they are useful for the treatment of inflammatory pain, for the treatment of hyperalgesia and, in particular, for the treatment of severe chronic pain. They are, for example, useful for the treatment of pain, inflammation and/or oedema consequential to trauma, e.g. associated with burns, sprains, fracture or the like, subsequent to surgical intervention, e.g. as post-operative analgesics, as well as for the treatment of inflammatory pain of diverse genesis, e.g. for the treatment of bone and joint pain (osteoarthritis), rheumatoid arthritis, rheumatic disease, teno-synovitis, gout, cancer pain, myofascial pain (muscular injury, fibromyalgia), chronic neuropathic pain, e.g. diabetic neuropathy, phantom limb pain and perioperative pain (general surgery, gynecologic surgery). They are further suitable as analgesics for the treatment of pain associated with, e.g., angina, menstruation or cancer. As anti-inflammatory/anti-oedema agents, they are further useful, e.g., for the treatment of inflammatory skin disorders, for example psoriasis and eczema.

The agents of the invention are also useful as smooth muscle relaxants, e.g. for the treatment of spasm of the gastro-intestinal tract or uterus, e.g. in the treatment of glaucoma/intra-ocular pressure, e.g. in the therapy of Crohn's disease, ulcerative colitis or pancreatitis and for the treatment of muscle spasticity and tremor in e.g. multiple sclerosis.

For the above indications the appropriate dosage of the agents of the invention will, of course, vary depending upon, for example, the host, the mode of administration and the nature and severty of the condition being treated as well as the relative potency of the particular an agent of the invention employed. For example, the amount of active agent required may be determined on the basis of known in vitro and in vivo techniques, determining how long a particular active agent concentration in the blood plasma remains at an acceptable level for a therapeutic effect. In general, satisfactory results in animals are indicated to be obtained at daily dosages of from about 0.01 to about 20.0 mg/kg p.o. In humans, an indicated daily dosage is in the range of from about 0.7 to about 1400 mg/day p.o., e.g. from about 50 to 200 mg (70 kg man), conveniently administered once or in divided doses up to 4× per day or in sustained release form. Oral dosage forms accordingly suitably comprise from about 1.75 or 2.0 to about 700 or 1400 mg. an agent of the invention admixed with an appropriate pharmaceutically acceptable diluent or carrier therefor.

The agents of the invention may alternatively be administered e.g. topically in the form of a cream, gel or the like for example for the treatment of conditions of the skin as hereinbefore described or by inhalation, e.g. in dry powder form, for example for the treatment of asthma.

Examples for compositions comprising an agent of the invention include, e.g. a solid dispersion, an aqueous solution, e.g. containing a solubilising agent, a microemulsion and a suspension of, e.g. a hydrochloride salt of a compound of formula I In the range of from 0.1 to 1%, e.g. 0.5%. The composition may be buffered to a pH in the range of, e.g. from 3.5 to 9.5, e.g. to pH 4.5, by a suitable buffer.

The agents of the invention are also useful as research chemicals.

The agents of the Invention can be administered in vivo either alone or in combination with other pharmaceutical agents effective in the treatment of diseases and conditions in which $CB_1$ receptor activation plays a role or is implicated including cyclooxygenase-2 (COX-2) inhibitors, such as specific COX-2 inhibitors (e.g. celecoxib and rofecoxib) and nonsteroidal anti-inflammatory drugs (NSAIDs) (e.g. acetylsalicylic acid, Propionic acid derivatives), vanilloid receptor antagonists, tricyclic antidepressants (e.g. Anafranil®, Asendin®, Aventyl®, Elavil®, Endep®, Norfranil®, Norpramin®, Pamelor®, Sinequan®, Surmontil®, Tipramine®, Tofranil®, Vivactil®, Tofranil-PM®), anticonvulsants (e.g. gabapentin), and $GABA_S$ agonists (e.g. L-baclofen).

The pharmaceutical compositions for separate administration of the combination partners and for the administration in a fixed combination, i.e. a single galenical composition comprising at least two combination partners, according to the invention can be prepared in a manner known per se and are those suitable for enteral, such as oral or rectal, and parenteral administration to mammals, including man, comprising a therapeutically effective amount of at least one pharmacologically active combination partner alone or in combination with one or more pharmaceutically acceptable carries, especially suitable for enteral or parenteral application.

Novel pharmaceutical composition contain, for example, from about 0.1% to about 99.9%, preferably from about 20% to about 60%, of the active ingredients. Pharmaceutical preparations for the combination therapy for enteral or parenteral administration are, for example, those in unit dosage forms, such as sugar-coated tablets, tablets, capsules or suppositories, and furthermore ampoules. If not indicated otherwise, these are prepared in a manner known per se, for example by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units.

In particular, a therapeutically effective amount of each of the combination partners may be administered simultaneously or sequentially and in any order, and the components may be administered separately or as a fixed combination. For example, the method of delay of progression or treatment of a proliferative disease according to the invention may comprise (i) administration of the combination partner (a) in free or pharmaceutically acceptable salt form and (ii) administration of a combination partner (b) in free or pharmaceutically acceptable salt form, simultaneously or sequentially in any order, in jointly therapeutically effective amounts, preferably in synergistically effective amounts, e.g. in daily dosages corresponding to the amounts described herein. The individual combination partners can be administered separately at different times during the course of therapy or concurrently in divided or single combination forms. Furthermore, the term administering also encompasses the use of a pro-drug of a combination partner that convert in vivo to the combination partner as such. The instant invention is therefore to be understood as embracing all such regimes of simultaneous or alternating treatment and the term "administering" is to be interpreted accordingly.

The effective dosage of each of the combination partners employed may vary depending on the particular compound or pharmaceutical composition employed, the mode of administration, the condition being treated, the severity of the condition being treated. Thus, the dosage regimen is selected in accordance with a variety of factors including the route of administration and the renal and hepatic function of the patient. A physician, clinician or veterinarian of ordinary skill can readily determine and prescribe the effective amount of the single active ingredients required to prevent, counter or arrest the progress of the condition. Optimal precision in achieving concentration of the active ingredients within the range that yields efficacy without toxicity requires a regimen based on the kinetics of the active ingredients' availability to target sites. In general, satisfactory results in animals are indicated to be obtained at daily dosages of from about 0.01 to about 20.0 mg/kg p.o. In humans, an indicated daily dosage is in the range of from about 0.7 to about 1400 mg/day p.o., e.g. from about 50 to 200 mg (70 kg man), conveniently administered once or in divided doses up to 4× per day or in sustained release form. Oral dosage forms accordingly suitably comprise from about 1.75 or 2.0 to about 700 or 1400 mg.

In accordance with the foregoing, the present invention also provides:

(1) An agent of the invention for use as a cannabinoid receptor agonist, for example for use in any of the particular indications hereinbefore set forth;

(2) A pharmaceutical composition comprising an agent of the invention as active ingredient together with a pharmaceutically acceptable diluent or carrier therefore. Such composition may be manufactured in conventional manner.

(2') A pharmaceutical composition for the treatment or prevention of a disease or condition in which cannabinoid receptor activation plays a role or is implicated comprising an agent of the invention and a carrier.

(3) A method for the treatment of any of particular indication hereinbefore set forth in a subject in need thereof which comprises administering an effective amount of an agent of the invention;

(3') A method for treating or preventing a disease or condition in which cannabinoid receptor activation plays a role or is implicated comprising administering to a mammal in need thereof a therapeutically effective amount of an agent of the invention.

(4) The use of an agent of the invention for the manufacture of a medicament for the treatment or prevention of a disease or condition in which cannabinoid receptor activation plays a role or is implicated;

(5) A method as defined above comprising co-administration, e.g. concomitantly or in sequence, of a therapeutically effective amount of a CB agonist, e.g. an agent of the invention and a second drug substance, said second drug substance being for example for use in any of the particular indications hereinbefore set forth.

(6) A combination comprising a therapeutically effective amount of a CB agonist, e.g. an agent of the invention and a second drug substance, said second drug substance being for example for use in any of the particular indications hereinbefore set forth.

The preferred compound of formula I for use in accordance with the invention is that of Example 1. This compound is a potent CB agonist, in particular $CB_1$ agonist, in vitro ($K_1$=0.015±0.004 µM). The $D_{50}$ value in the neuropathic pain model of test 11 for the compound of example 1 is 0.18 mg/kg p.o.

| Abbreviations used in the examples: | |
|---|---|
| BINAP | 2,2'-Bis(diphenylphosphino)-1,1'-binaphthyl |
| DCM | Dichloromethane |
| DIAD | Diisopropyl azodicarboxylate |
| DIEA | N,N-Diisopropylethylamine |
| DMAP | 4-Dimethylaminopyridine |
| DMF | Dimethylformamide |
| DMSO | Dimethylsulfoxide |
| DPEphos | Bis[(2-diphenylphosphino)phenyl]ether |
| DPPA | Diphenylphophoryl azide |
| MCPBA | m-Chloroperbenzoic acid |
| MS 4Å | Molecular sieves 4Å |
| $PdCl_2dppf \cdot CH_2Cl_2$ | 1,1'-Bis(diphenylphosphino)ferrocene dichloro palladium (II) dichloromethane complex |
| $Pd_2dba_3$ | Tris(dibenzylideneacetone)dipalladium (0) |
| $Pd(PPh_3)_4$ | Tetrakis(triphenylphosphine)palladium (0) |
| THF | Tetrahydrofuran |
| t-BuOK | potassium tert-butoxide |

The following examples illustrate the invention.

EXAMPLE 1

Preparation f naphthalen-1-yl-(4-pentyloxy-naphthalen-1-yl)-methan ne (a) 20 g of 1 -naphthol, 21.2 ml $NEt_3$ and 1,7 g of 4-dimethylaminopyridine are dissolved in 300 ml methylene chloride at RT. The solution is cooled to 10° C. 20.9 ml of naphthoyl chloride in 100 ml methylene chloride is added dropwise within 15 min. Conventional workup affords naphthalen-1-yl-(naphthalenoxy-1-yl)-methanone.

(b) 29.0 g of naphthalen-1-yl-(naphthalenoxy-1-yl)-methanone is added in portions to a suspension of 14.3 g aluminium chloride in 100 ml toluene and stirred for 2 h at 140° C. Conventional workup affords naphthalen-1-yl-(4-hydroxy-naphthalen-1-yl)-methanone.

(c) 11.0 g of naphthalen-1-yl-(4-hydroxy-naphthalen-1-yl)-methanone and 6.1 g of potassium carbonate in 130 ml of acetone are stirred for 15 min at reflux. Then, within 2 min, a solution of 6.8 ml 1-bromopentane in 20 ml of acetone is added and the suspension is stirred for additional 22 h at reflux. Conventional workup and subsequent chromatography affords naphthalen-1-yl-(4-pentyloxy-naphthalen-1-yl)-methanone.

Melting point: 72–75° C. (Propan-2-ol); HPLC retention time (min): 8.15 [HPLC Method:

Kingsorb 3 micron C18 column (30×4.6 mm). Gradient elution: 10–100% acetonitrile in 0.1% trifluoroacetic acid in water over 7 minutes, then 100% acetonitrile over 3 minutes.]

$^1$H NMR (400 MHz, $CDCl_3$): δ9.02 (d, 1H), 8.43 (d, 1H), 8.25 (d, 1H), 8.01 (d, 1H), 7.95 (d, 1H), 7.70 (t, 1H), 7.62–7.50 (m, 6H), 6.68 (d, 1H), 4.19 (t, 2H), 2.0–1.94 (m, 2H), 1.6–1.54 (m, 2H), 1.49–1.44 (m, 2H), 0.99 (t, 3H).

MS m/z (%): 369.1 (M+H, 100); IR (v, $cm^{-1}$): 1633 (C=O)

In the following examples compounds of formula I wherein $R^2$ is —O—$(CH_2)_4CH_3$ are prepared according to the invention (Ex.=Example).

| Ex. | X | $R^1$ | $R^3$ |
|---|---|---|---|
| 2 | —S— | naphthyl | H |
| 3 | —S(O)— | naphthyl | H |
| 4 | —S(O)$_2$— | naphthyl | H |
| 5 | —P(O)(OCH$_3$)— | naphthyl | H |
| 6 | —P(O)(OH)— | naphthyl | H |
| 7 | —S(O)— | 4-methoxyphenyl | H |
| 8 | —S(O)$_2$— | 4-methoxyphenyl | H |
| 9 | —S(O)— | 4-acetamidophenyl | H |
| 10 | —S(O)$_2$— | 4-acetamidophenyl | H |
| 11 | —S(O)$_2$— | 1,2,3,4-tetrahydroquinolin-1-yl | H |
| 12 | —S— | 4-acetamidophenyl | H |
| 13 | —S(O)$_2$NH— | 5,7-dimethyl-2,1,3-benzothiadiazol-4-yl | H |
| 14 | —P(O)(OH)— | 4-methoxyphenyl | H |
| 15 | —P(O)(OH)— | 4-thiomethylphenyl | H |
| 16 | —P(O)(OCH$_3$)— | quinolin-8-yl | H |
| 17 | —S— | 3,4-dimethoxyphenyl | H |
| 18 | —S(O)— | 3,4-dimethoxyphenyl | H |
| 19 | —S(O)$_2$— | 3,4-dimethoxyphenyl | H |
| 20 | —P(O)(OCH$_3$)— | indol-7-yl | H |
| 21 | —P(O)(OH)— | quinolin-8-yl | H |
| 22 | —S(O)$_2$— | 6-methoxy-1,2,3,4-tetrahydroquinolin-1-yl | H |
| 23 | —P(O)(OH)— | indol-7-yl | H |
| 24 | —NH— | naphthyl | H |
| 25 | —S(O)$_2$NH— | naphthyl | H |
| 26 | —N(CH$_3$)— | naphthyl | H |
| 27 | —C(O)O— | naphthyl | H |
| 28 | —NH— | 4-methoxyphenyl | H |
| 29 | —CH(OH)— | naphthyl | H |
| 30 | —CH=N— | naphthyl | H |
| 31 | —CH=CH— | naphthyl | H |
| 32 | —C(O)O— | 1,2,3,4-tetrahydronaphthalen-5-yl | H |
| 33 | —C(O)O— | indan-4-yl | H |
| 34 | —CH$_2$NH— | naphthyl | H |
| 35 | —C(O)O— | 5-chloro-2,1,3-benzothiadiazol-4-yl | H |
| 36 | —C(O)O— | isoquinolin-5-yl | H |
| 37 | —C(O)O— | quinolin-5-yl | H |
| 38 | —C(O)O— | quinolin-8-yl | H |
| 39 | —NHC(O)NH— | naphthyl | H |
| 40 | —NHC(O)— | 1,2,3,4-tetrahydroquinolin-1-yl | H |

-continued

| Ex. | X | R¹ | R³ |
|---|---|---|---|
| 41 | —NHC(O)— | 6-methoxy-1,2,3,4-tetrahydroquinolin-1-yl | H |
| 42 | —CH₂NH— | (5,7-dimethyl)-2,1,3-benzothiadiazol-4-yl | H |
| 43 | —CH₂NH— | 2,1,3-benzothiadiazol-4-yl | H |
| 44 | —CH₂NH— | 2,1,3-benzoxadiazol-4-yl | H |
| 45 | —C(NH)— | 4-methoxynaphthyl | H |

-continued

| Ex. | X | R¹ | R³ |
|---|---|---|---|
| 46 | —C(O)O— | 1,2,3,4-tetrahydroquinolin-8-yl | H |
| 47 | —CH(OH)— | naphthyl | 3-C(O)OCH₃ |

The following examples of compounds of formula I wherein X is C(O) are prepared according to the invention:

| No. | R¹ | R² | R³ |
|---|---|---|---|
| 48 | naphthyl | —O—(CH₂)₃CH₃ | 8-OH |
| 49 | naphthyl | —O—(CH₂)₃CH₃ | 8-OC(O)-naphthyl |
| 50 | naphthyl | —O—(CH₂)₄CH₃ | 6-N-(CH₂CH=CH₂)₂ |
| 51 | naphthyl | —O—(CH₂)₄CH₃ | 6-NHCH₂CH=CH₂ |
| 52 | naphthyl | —O—(CH₂)₄CH₃ | 7-OC(O)-naphthyl |
| 53 | naphthyl | —O—(CH₂)₄CH₃ | 7-OC(O)-methyl |
| 54 | naphthyl | —O—(CH₂)₄CH₃ | 7-OH |
| 55 | naphthyl | —O—(CH₂)₄CH₃ | -7-OCH₂C(O)OCH₃ |
| 56 | naphthyl | —O—(CH₂)₄CH₃ | -7-OCH₂C(O)OH |
| 57 | naphthyl | —O—(CH₂)₄CH₃ | 6-NH₂ |
| 58 | naphthyl | —O—(CH₂)₄CH₃ | 7-OCH₂C(O)NHNHC(O)CH₃ |
| 59 | naphthyl | —O—(CH₂)₄CH₃ | 7-[O—CH₂-(2-methyl)-1,3,4-oxadiazol-5-yl] |
| 60 | naphthyl | —O—(CH₂)₄CH₃ | 7-(4-methylpiperazin-1-yl) |
| 61 | naphthyl | —O—(CH₂)₄CH₃ | 7-(piperazin-1-yl) |
| 62 | naphthyl | —O—(CH₂)₄CH₃ | 7-NH₂ |
| 63 | naphthyl | —O—(CH₂)₄CH₃ | 6-N(CH₃)₂ |
| 64 | naphthyl | —O—(CH₂)₄CH₃ | 7-N(CH₃)₂ |
| 65 | naphthyl | —O—(CH₂)₄CH₃ | 7-cyano |
| 66 | naphthyl | —O—(CH₂)₄CH₃ | 7-(1H-tetrazol-5-yl) |
| 67 | naphthyl | —O—(CH₂)₄CH₃ | 7-OCH₃ |
| 68 | naphthyl | —O—(CH₂)₄CH₃ | 7-(1-methyltetrazol-5-yl) |
| 69 | naphthyl | —O—(CH₂)₄CH₃ | 7-(2-methyltetrazol-5-yl) |
| 70 | naphthyl | —O—(CH₂)₄CH₃ | 7-C(O)NH₂ |
| 71 | naphthyl | —O—(CH₂)₄CH₃ | 7-C(O)OH |
| 72 | naphthyl | —O—(CH₂)₄CH₃ | 3-C(O)OCH₃ |
| 73 | naphthyl | —O—(CH₂)₄CH₃ | 3-C(O)OH |
| 74 | naphthyl | —O—(CH₂)₄CH₃ | 7-(2-methyl-1,3,4-oxadiazol-5-yl |
| 75 | naphthyl | —O—(CH₂)₄CH₃ | 3-C(O)NHCH₂C(O)OH |
| 76 | 4-fluoronaphthyl | —O—(CH₂)₄CH₃ | 7-OC(O)CH₃ |
| 77 | 4-fluoronaphthyl | —O—(CH₂)₄CH₃ | 7-OH |
| 78 | 4-(1,2,4-triazol-1-yl)-naphthyl | —O—(CH₂)₄CH₃ | 7-OH |

The following examples of compounds of formula I wherein X is C(O) and R³ is hydrogen are prepared according to the invention:

| No. | R¹ | R² |
|---|---|---|
| 79 | 8-hydroxy-1,2,3,4-tetrahydroquinolin-1-yl | —O—(CH₂)₄CH₃ |
| 80 | 1,2,3,4-tetrahydroquinolin-1-yl | —O—(CH₂)₄CH₃ |
| 81 | naphthyl | —O—(CH₂)₄CH₃ |
| 82 | 4-nitro-naphth-1-yl | —O—(CH₂)₄CH₃ |
| 83 | 4-amino-naphth-1-yl | —O—(CH₂)₄CH₃ |
| 84 | 4-dimethylamino-naphth-1-yl | —O—(CH₂)₄CH₃ |
| 85 | 4-methoxy-naphth-1-yl | —O—(CH₂)₄CH₃ |
| 86 | 3-nitro-naphth-1-yl | —O—(CH₂)₄CH₃ |
| 87 | 3-amino-naphth-1-yl | —O—(CH₂)₄CH₃ |
| 88 | quinolin-4-yl | —O—(CH₂)₄CH₃ |
| 89 | quinolin-3-yl | —O—(CH₂)₄CH₃ |
| 90 | quinolin-2-yl | —O—(CH₂)₄CH₃ |
| 91 | 3-(dimethylamino)naphthyl | —O—(CH₂)₄CH₃ |
| 92 | quinolin-8-yl | —O—(CH₂)₄CH₃ |
| 93 | isoquinolin-1-yl | —O—(CH₂)₄CH₃ |
| 94 | 4-fluoro-naphthyl | —O—(CH₂)₄CH₃ |

-continued

| No. | R¹ | R² |
|---|---|---|
| 95 | 4-cyanonaphthyl | —O—(CH$_2$)$_4$CH$_3$ |
| 96 | 4-(1,2,4-triazol-1-yl)-naphthyl | —O—(CH$_2$)$_4$CH$_3$ |
| 97 | 4-1H-tetrazol-5-yl-naphthyl | —O—(CH$_2$)$_4$CH$_3$ |
| 98 | 4-(4-hydroxy)butoxy-naphthyl | —O—(CH$_2$)$_4$CH$_3$ |
| 99 | 4-pentoxy-naphthyl | —O—(CH$_2$)$_4$CH$_3$ |
| 100 | 4-(2-morpholin-1-yl)ethoxynaphthyl | —O—(CH$_2$)$_4$CH$_3$ |
| 101 | 3-methylsulfonamido-naphthyl | —O—(CH$_2$)$_4$CH$_3$ |
| 102 | 4-methylsulfonamido-naphthyl | —O—(CH$_2$)$_4$CH$_3$ |
| 103 | 4-(pyrazol-1-yl)-naphthyl | —O—(CH$_2$)$_4$CH$_3$ |
| 104 | 4-(imidazol-1-yl)-naphthyl | —O—(CH$_2$)$_4$CH$_3$ |
| 105 | 4-carboxynaphthyl | —O—(CH$_2$)$_4$CH$_3$ |
| 106 | 4-aminocarbonylnaphthyl | —O—(CH$_2$)$_4$CH$_3$ |
| 107 | 4-hydroxynaphthyl | —O—(CH$_2$)$_4$CH$_3$ |
| 108 | 4-(C(NH2)=NOH)-naphthyl | —O—(CH$_2$)$_4$CH$_3$ |
| 109 | naphthyl | 2-(morpholin-4-yl)-ethoxy |
| 110 | naphthyl | —O—(CH$_2$)$_3$CH$_3$ |
| 111 | naphthyl | —O—(CH$_2$)$_2$CH$_3$ |
| 112 | naphthyl | 2-(piperidin-1-yl)-ethoxy |
| 113 | naphthyl | 2-(4-methoxyphenyl)-ethoxy |
| 114 | naphthyl | 2-(phenyl)-ethoxy |
| 115 | naphthyl | 2-(4-nitrophenyl)-ethoxy |
| 116 | naphthyl | 2-(4-dimethylaminophenyl)-ethoxy |
| 117 | naphthyl | 2-(aminophenyl)-ethoxy |
| 118 | naphthyl | 3-(morpholin-4-yl)-propyloxy |
| 119 | naphthyl | 2-(2-nitrophenyl)-ethoxy |
| 120 | naphthyl | —NH—(CH$_2$)$_3$CH$_3$ |
| 121 | naphthyl | —O—(CH$_2$)$_4$C(O)OCH$_2$CH$_3$ |
| 122 | naphthyl | —O—(CH$_2$)$_3$C(O)OCH$_2$CH$_3$ |
| 123 | naphthyl | 2-(2-aminophenyl)-ethoxy |
| 124 | naphthyl | 2-(2-dimethylaminophenyl)-ethoxy |
| 125 | naphthyl | 3-(piperidin-1-yl)-propyloxy |
| 126 | naphthyl | —N—[2-(morpholin-4-yl)-ethyl]—N—(CH$_2$)$_3$CH$_3$ |
| 127 | naphthyl | —NH—(CH$_2$)$_4$CH$_3$ |
| 128 | naphthyl | —O—(CH$_2$)$_3$OH |
| 129 | naphthyl | —O—(CH$_2$)$_5$OH |
| 130 | naphthyl | —O—(CH$_2$)$_4$OH |
| 131 | naphthyl | —O—(CH$_2$)$_5$CH$_3$ |
| 132 | naphthyl | —O—(CH$_2$)$_6$CH$_3$ |
| 133 | naphthyl | —N—(CH$_3$)(CH$_2$)$_3$CH$_3$ |
| 134 | naphthyl | —N—(CH$_3$)(CH$_2$)$_4$CH$_3$ |
| 135 | naphthyl | —O—(CH$_2$)$_2$OCH$_2$CH$_3$ |
| 136 | naphthyl | —O—CH$_2$C(O)OCH$_3$ |
| 137 | naphthyl | —O—CH$_2$-(2-methyl)-oxadiazol-5-yl |
| 138 | naphthyl | —O—CH$_2$-(2-ethyl)-oxadiazol-5-yl |
| 139 | naphthyl | —O—CH$_2$-(2-propyl)-oxadiazol-5-yl |
| 140 | naphthyl | —O—(CH$_2$)$_3$CH(CH$_3$)$_2$ |
| 141 | naphthyl | —NHC(O)(CH$_2$)$_3$CH$_3$ |
| 142 | naphthyl | O—CH$_2$CH=CHCH$_2$CH$_3$ (Z) |
| 143 | naphthyl | O—CH$_2$CH=CHCH$_2$CH$_3$ (E) |
| 144 | phenyl | —O—(CH$_2$)$_3$CH$_3$ |
| 145 | 2-hydroxy-3-methoxyphenyl | —O—(CH$_2$)$_3$CH$_3$ |
| 146 | 2,3-dimethoxyphenyl | —O—(CH$_2$)$_3$CH$_3$ |
| 147 | 4-(butoxy)phenyl | H |
| 148 | 4-[2-(morpholin-4-yl)ethoxy]phenyl | H |
| 149 | 4-[3-(hydroxy)propoxy]phenyl | H |
| 150 | 2-methyl-7-pentoxy-benzimidazol-4-yl | H |
| 151 | 7-pentoxybenzimidazol-4-yl | H |
| 152 | 7-pentoxy-benzotriazol-4-yl | H |
| 153 | 3-(NHC(O)NHOCH$_3$)-4-pentoxyphenyl | H |
| 154 | 2-oxo-7-pentoxy-1,3-dihydro-benzimidazol-4-yl | H |
| 155 | 2-(NHCH$_2$phenyl)-7-pentoxy-benzimidazol-4-yl | H |
| 156 | 2-(NHCH$_2$cyclohexyl)-7-pentoxy-benzimidazol-4-yl | H |
| 157 | 2-(NH(CH$_2$)$_3$N(CH$_2$CH$_3$)$_2$)-7-pentoxy-benzimidazol-4-yl | H |
| 158 | 2-(NH(CH$_2$)$_3$CH$_3$)-7-pentoxy-benzimidazol-4-yl | H |
| 159 | 2-(4-methylpiperazin-1-yl)-7-pentoxy-benzimidazol-4-yl | H |
| 160 | 2-(NH(CH$_2$)$_2$OH)-7-pentoxy-benzimidazol-4-yl | H |

-continued

| No. | R¹ | R² |
|---|---|---|
| 161 | 2-(NH(CH$_2$)$_2$O(CH$_2$)$_2$OH)-7-pentoxy-benzimidazol-4-yl | H |
| 162 | 2-oxo-3-methoxy-7-pentoxy-1,3-dihydro-benzimidazol-4-yl | H |

The following examples of compounds of formula I wherein X is C(O) are prepared according to the invention:

| | R1 | R2 | R3 |
|---|---|---|---|
| 163 | 4-(imidazol-1-yl)-naphtyl | —O—(CH$_2$)$_4$CH$_3$ | 7-OH |

In particular the compounds are prepared according to the following Preparations:

The preparation 1: Synthesis of Ketones

Preparation is done according to example 1 and further applicable to examples: 29, 81, 109, 110, 111, 112, 113, 114, 115, 116, 117, 118, 119, 121, 122, 123, 124, 125, 128, 129, 130, 131, 132, 135, 136, 137, 138, 139, 140, 142, 143, 144, 147, 148, 149.

EXAMPLE 2

Synthesis of Sulfides, Sulfones and Sulfoxides

Applicable to EX: 2, 3, 4, 7, 8, 9, 10, 12, 17, 18, 19.

(a) 1-Iodo-4-pentyloxy-naphthalene: A solution of 1-pentyloxy-naphthalene (6.41 g, 29.9 mmol) in acetonitrile (120 mL) is treated with N-iodosuccinimide (10.1 g, 44.9 mmol) and stirred for 6 h at 82° C. After cooling to room temperature, the reaction mixture is distributed between 1M KHCO$_3$ (185 mL) and toluene (2×185 mL). The organic phase is washed with water, dried over Na$_2$SO$_4$ and concentrated. Flash chromatography (cyclohexane) yielded 9.0 g (89%) of slightly reddish crystals. EI-MS (m/z) 340 (M$^+$).

(b) 1-(1-Naphthalenesulfanyl)-4-pentyloxy-naphthalene: A mixture of 1-iodo-4-pentyloxy-naphthalene (0.68 g, 2.0 mmol), t-BuOK (0.40 g, 3.0 mmol), 1-naphthylthiol (0.48 g, 3.0 mmol), DPEphos (120 mg), and Pd$_2$dba$_3$ (80 mg) in toluene (16 mL) is heated for 2 h at 90° C. After cooling to room temperature, the reaction mixture is washed with water (16 mL) and filtered over Hyflo. The organic phase is dried over Na$_2$SO$_4$ and concentrated. Flash chromatography (cyclohexane/acetone) yielded 0.62 g (80%) of colourless crystals.

(c) 1-(1-Naphthalenesulfinyl)4-pentyloxy-naphthalene: A solution of 1-(1-naphthalenesulfanyl)-4-pentylox-naphthalene (112 mg, 0.3 mmol) in DCM (3 mL) is stirred with MCPBA (74 mg, 0.3 mmol) for 2 h at 0° C. The reaction mixture is distributed between DCM (3 mL) and 1M KHCO$_3$ (6 mL). The organic phase is washed with water (3 mL), dried over Na$_2$SO$_4$ and concentrated. Flash chromatography (cyclohexane/acetone) yielded 94 mg (80%) of colourless crystals.

(d) 1-(1-Naphthylsulfonyl)4-pentyloxy-naphthalene: A solution of 1-(1-naphthalenesulfanyl)-4-pentyloxy-naphthalene (112 mg, 0.3 mmol) in DCM (3 mL) is stirred with MCPBA (148 mg, 0.9 mmol) for 2 h at 0° C. and further 2 h at room temperature. The reaction mixture is distributed between DCM (3 mL) and 1M KHCO$_3$ (6 mL). The organic phase is washed with water (3 mL), dried over Na$_2$SO$_4$ and concentrated. Flash chromatography (cyclohexane/acetone) yielded 91 mg (73%) of colourless crystals.

EXAMPLE 3

Synthesis of Phosphinic Acid Esters

Applicable to Ex. 5, 6, 14, 15, 16, 20, 21, 23.

(a) (4-Pentyloxy-naphthalen-1-yl)-phosphinic acid methyl ester: A solution of dry, crystalline H$_3$PO$_2$ (1.46 g, 21.9 mmol) in toluene/THF (1:1, 11 mL) is treated with HC(OMe)$_3$ (9.6 mL, 87.7 mmol) and stirred for 1 h at 0° C. and further 2 h at room temperature. The mixture is added to a solution of 1-iodo-4-pentyloxy-naphthalene (3.65 g, 10.7 mmol) and NEt$_3$ (1.64 mL, 11.8 mmol) in acetonitrile (27 mL). After addition of (Ph$_3$P)$_2$PdCl$_2$ (376 mg, 0.54 mmol) the reaction mixture is heated at 90° C. for 4 h. After cooling to room temperature, the reaction mixture is concentrated. Flash chromatography (DCM/methanol) yields 2.16 g (69%) of a brownish oil. EI-MS (m/z) 292 (M$^+$).

(b) Naphthalen-1-yl-(4-pentyloxy-naphthalen-1-yl)-phosphinic acid methyl ester: A mixture of (4-pentyloxy-naphthalen-1-yl)-phosphinic acid methyl ester (339 mg, 1.2 mmol), NEt$_3$ (0.18 mL, 1.3 mmol), 1-naphthyliodide (0.17 mL, 1.2 mmol), DPEphos (81 mg), and Pd$_2$dba$_3$ (60 mg) in acetonitrile (3 mL) is heated at 90° C. for 3 h. After cooling to room temperature, the reaction mixture is distributed between water (6 mL) and toluene (2×6 mL). The combined organic phases are washed with water (6 mL), dried over Na$_2$SO$_4$ and concentrated. Flash chromatography (DCM/methanol) yields 246 mg (50%) of a slightly yellow oil.

(c) Naphthalen-1-yl-(4-pentyloxy-naphthalen-1-yl)-phosphinic acid: A solution of naphthalen-1yl-(4-pentyloxy-naphthalen-1-yl)-phosphinic acid methyl ester (156 mg, 0.38 mmol) in acetonitrile (1.5 mL) is treated with trimethylsilyl iodide (0.1 mL, 0.75 mmol) and stirred at room temperature for 1 h. The reaction mixture is distributed between 1M Na$_2$CO$_3$ (4 mL) and toluene (4 mL). The water phase is acidified with HCl solution (1.5 mL) and extracted with toluene (2×4 mL). The combined extracts are dried over Na$_2$SO$_4$ and concentrated. Flash chromatography (DCM/methanol/NH$_3$) yields 127 mg (83%) of a colourless foam.

EXAMPLE 4

Synthesis of Amines

Applicable to Ex: 24, 26, 28.

(a) Naphthalen-1-yl-(4-pentyloxy-naphthalen-1-yl) amine: A mixture of 1-iodo4-pentyloxy-naphthalene (1.02 g, 3.0 mmol), t-BuONa (0.29 g, 4.2 mmol), 1-naphthylamine (0.43 g, 3.6 mmol), 2-(di-t-butylphosphino)biphenyl (53.7 mg), and Pd$_2$dba$_3$ (155.3 mg) in toluene (6 mL) is heated for 40 min at 80° C. After cooling to room temperature the reaction mixture is filtered over silica and concentrated.

Flash chromatography (cyclohexane/ethyl acetate) yields 0.85 g (2.4 80%) of colourless crystals.

(b) Methyl-naphthalen-1-yl-(4-pentyloxy-naphthalen-1-yl)-amine: A solution of naphthalen-1-yl-(4-pentyloxy-naphthalen-1-yl)-amine (154 mg, 0.40 mmol) in DMF (1.7 mL) is treated with NaH (75%,18 mg, 0.56 mmol) and methyl iodide (0.13 mL, 2.2 mmol) and stirred at 50° C. for 18 h. After cooling to room temperature, the reaction mixture is distributed between water (4 mL) and toluene (2×4 mL). The combined organic phases are dried over $Na_2SO_4$ and concentrated. Flash chromatography (cyclohexane/ethyl acetate) yielded 70 mg (48%) of a light brown foam.

EXAMPLE 5

Synthesis of Sulfonamides

Applicable to Ex 11, 13, 22, 25.

(a) 4-Pentyloxy-naphthalene-1-sulfonic acid, sodium salt: A mixture of 4-hydroxy-naphthalene-1-sulfonic acid (14.07 g, 40 mmol), NaOH (3.2 g, 80 mmol), npentylbromide (10 mL, 80 mmol) and DMSO (200 mL) is stirred at 60° C. for 2h. After cooling to room temperature the reaction mixture is treated with water (400 mL) and neutralised with 6N HCl (15 mL). After stirring at 0° C. for 30 min the product is collected by filtration, washed with water and dried in vacuo to afford 12.6 g (100%) of colourless crystals. mp 275–285° C.

(b) 1-(4-Pentyloxy-naphthalene-1-sulfonyl)-1,2,3,4-tetrahydroquinoline: A mixture of 4-pentyloxy-naphthalene-1-sulfonic acid, sodium salt (147 mg, 0.5 mmol) and DCM (3 mL) is treated with thionyl chloride (43 μL, 0.6 mmol) and stirred at room temperature for 30 min. The resulting clear solution is treated with DIEA (86 μL, 0.5 mmol) and 1,2,3,4-tetrahydroquinoline (95 μL, 0.75 mmol) and stirred at room temperature for 18 h. The reaction mixture is distributed between water (3 mL) and DCM (2×3 mL). The organic phase is washed with water (3 mL), dried over $Na_2SO_4$ and concentrated. Flash chromatography (toluene) yields 79 mg (39%) of a colourless oil.

EXAMPLE 6

Synthesis of Amides

Applicable to Ex. 79, 80, 163.

(a) 4-Pentyloxy-naphthalene-1-carbaldehyde: A mixture of 4-hydroxy-naphthalene-1-carbaldehyde (1.72 g, 10 mmol), NaOH (0.48 g, 12 mmol), n-pentylbromide (1.5 mL, 12 mmol) and DMSO (10 mL) is stirred at 50° C. for 4 h. After cooling to room temperature the reaction mixture is treated with water (20 mL) and 2N HCl (1.5 mL, pH4). After extraction with toluene (2×20 mL), the combined organic phases are washed with water, dried over $Na_2SO_4$ and concentrated. Crystallization (cyclohexane) yields 2.15 g (89%) of brownish crystals. mp 67–68° C.

(b) 4-Pentyloxy-naphthalene-1-carboxylic acid: A solution of 4-pentyloxy-naphthalene-1-carbaldehyde (1.9 g, 7.8 mmol) and 2-methyl-2-butene (39 mL) in t-BuOH (150 mL) is treated with a solution of $NaClO_2$ (7.05 g, 78 mmol) and $NaH_2PO_4.H_2O$ (7.53 g, 55 mmol) in water (62 mL). After stirring at room temperature for 17 h the product is collected by filtration, washed with water and dried in vacuo to afford 1.92 g (95%) of brownish crystals. mp 190–202° C.

(c) (3,4-Dihydro-2H-quinolin-1-yl)-(4-pentyloxy-naphthalen-1-yl)-methanone: A mixture of 4-pentyloxy-naphthalene-1-carboxylic acid (103 mg, 0.4 mmol) and DCM (2 mL) is treated with thionyl chloride (34.6 μL, 0.48 mmol) and DMF (0.2 mL) and stirred at 40° C. for 1 h. The resulting clear solution is treated with DIEA (103 μL, 0.6 mmol), 1,2,3,4-tetrahydroquinoline (80 mg, 0.6 mmol) and DMAP (4.9 mg, 0.04 mmol). After refluxing at 42° C. for 3 h the reaction mixture is distributed between 1M $KHCO_3$ (4 mL) and DCM (2×4 mL). The combined organic phases are washed with water, dried over $Na_2SO_4$ and concentrated. Flash chromatography (cyclohexane/acetone) yields 78 mg (52%) of greenish crystals.

EXAMPLE 7

Synthesis of Esters

Applicable to Ex: 27, 32, 33, 35, 36, 37, 38, 46

4-Pentyloxy-naphthalene-1-carboxylic acid naphthalen-1-yl ester: A solution of 4-pentyloxy-naphthalene-1-carbaldehyde (121 mg,.0.5 mmol) in $CCl_4$ (2 mL) is treated with t-BuOCl (8.82 M, 170 μL, 1.5 mmol) and stirred at 50° C. for 1 h. After addition of DIEA (0.3 mL, 1.7 mmol) and 1-naphthol (216 mg, 1.5 mmol) the mixture is refluxed for 2 h and distributed between 1M $KHCO_3$ (5 mL) and DCM (2×5 mL). The combined organic phases are dried over $Na_2SO_4$ and concentrated. Flash chromatography (cyclohexane/acetone) yields 82 mg (43%) of colourless crystals.

EXAMPLE 8

Synthesis of Imines and Amines

Applicable to Ex: 30, 34, 42, 43, 44.

(a) Naphthalen-1-yl-[1-(4-pentyloxy-naphthalen-1-yl)-methylidene]-amine: A solution of 4-pentyloxy-naphthalene-1-carbaldehyde (48.5 mg, 0.2 mmol), 1-naphthylamine (28.6 mg, 0.2 mmol) in DCM (1 mL) is treated with MS 4 Å (80 mg) and stirred at room temperature for 2 d. The mixture is filtered over Hyflo, dried over $Na_2SO_4$ and concentrated. Flash chromatography (cyclohexane/ethyl acetate) yields 60 mg (82%) of yellow crystals.

(b) Naphthalen-1-yl-(4-pentyloxy-naphthalen-1-ylmethyl)-amine: A solution of naphthalen-1-yl[1-(4-pentyloxy-naphthalen-1-yl)-methylidene]-amine (24 mg, 0.07 mmol) and $BH_3$ pyridine (16.3 μL, 0.13 mmol) in THF (0.65 mL) is stirred at room temperature for 16 h. The reaction mixture is concentrated and distributed between water (2 mL) and DCM (2 mL). The organic phase is dried over $Na_2SO_4$ and concentrated. Flash chromatography (cyclohexane/acetone) yields 14 mg (58%) of a colourless oil.

EXAMPLE 9

Synthesis of Ureas

Applicable to Ex: 39, 40, 41.

1-Naphthalen-1-yl-3-(4-pentyloxy-naphthalen-1-yl)-urea: A solution of 4-pentyloxy-naphthalene-1-carboxylic acid (103 mg, 0.4 mmol) and 1,8-bis(dimethylamino)naphthalene (86 mg, 0.4 mmol) in THF (0.8 mL) is stirred at room temperature for 30 min. After addition of DPPA (86 μL, 0.4 mmol) and 1-naphthylamine (229 mg, 1.6 mmol) the mixture is heated at 100° C. for 6 h, distributed between 2M HCl (8 mL) and DCM (2×8 mL). The combined organic phases are washed with 1 M $Na_2CO_3$ and water, dried over Na₂SO₄ and concentrated. Flash chromatography (cyclohexane/acetone) yields 78 mg (49%) of brownish crystals.

EXAMPLE 10

Friedel-Crafts Synthesis of Bis-Aryl Ketones

Applicable to Ex: 48, 49, 82, 83, 84, 85, 86, 87, 88, 89, 90, 91, 94, 95, 96, 97, 98, 99, 100, 101, 102, 103, 104, 105, 106, 107, 108, 141, 145, 146.

(4-Fluoronaphthalen-1-yl)-(4-pentyloxynaphthalen-1-yl) methanone: A stirred solution of 4-fluoro-1-naphthoic acid (0.5 g, 2.63 mmol) in anhydrous DCM (10 mL) is treated at room temperature with oxalyl chloride (0.52 g, 4.1 mmol) followed by a few drops of anhydrous DMF. Once bubbling subsided, the clear solution is cooled to 4° C. in an ice bath, and aluminium chloride (0.7 g, 5.25 mmol) is added in one portion. After stirring at 4° C. for 20 min, 1-pentyloxynaphthalene (0.563 g, 2.63 mmol) is added, and the reaction mixture is allowed to warm gradually to ambient temperature overnight. The reaction mixture is distributed between ethyl acetate (50 mL) and water (250 mL) and extracted. The aqueous phase is additionally washed with fresh ethyl acetate (2×50 mL). The combined organic phases are dried (anhydrous MgSO₄), filtered and concentrated in vacuo. The residue is purified by chromatography on silica gel using a Biotage apparatus (Dyax Corp.) and cyclohexane:ethyl acetate (9:1) as eluant to give the desired product (0.996 g, 98%).

EXAMPLE 11

Synthesis of Alkylamino Bis-Aryl Ketones

Applicable to Ex: 60, 61, 64, 120, 126, 127, 133, 134.

(a) Trifluoromethanesulfonic acid 4-(naphthalene-1-carbonyl)-naphthalen-1-yl ester: Trifluoro-methanesulfonic anhydride (3.1 mL, 18.43 mmol) is added slowly to a solution of (4-hydroxynaphthalen-1-yl)-naphthalen-1-yl methanone (5.0 g, 16.76 mmol) in pyridine (15 mL) at 0° C. under inert atmosphere. The reaction mixture is stirred at 0° C. for 30 min and then allowed to warm to ambient temperature over 24 h. The reaction mixture is poured into water and extracted three times with DCM. The combined organic extracts are washed sequentially with water, dilute aqueous HCl solution, water and brine. The organic phase is dried over anhydrous MgSO₄ and concentrated in vacuo. The residue is purified by flash chromatography (10% ether/cyclohexane) to afford the desired product (5.56 g, 77%).

(b) Naphthalen-1-yl-(4-butylaminonaphthalen-1-yl)methanone: A solution of trifluoromethanesulfonic acid 4-(naphthalene-1 carbonyl)-naphthalen-1 -yl ester (308 mg, 0.716 mmol) and n-butylamine (62.8 mg, 0.859 mmol) in anhydrous toluene (3 mL) is added to a mixture of palladium (II) acetate (3.2 mg, 0.014 mmol), BINAP (10 mg, 0.016 mmol) and sodium t-butoxide (96 mg, 1.002 mmol) under inert atmosphere. The mixture is heated at 80° C. for 4 h. Upon cooling, the mixture is diluted with ethyl acetate and filtered through Celite filter aid. The filtrate is evaporated in vacuo to afford a reddish-brown solid residue. This is purified by flash chromatography (10% ether/cyclohexane) to yield the desired product (85 mg, 34%) and 30 mg of recovered starting material.

(c) [4-{Butyl-(2-morpholin-4-ylethyl)amino}-naphthalen-1-yl]-naphthalen-1-yl methanone: A solution of naphthalen-1-yl-(4-butylaminonaphthalen-1-yl) methanone (65 mg, 0.18 mmol) in anhydrous DMF (4 mL) under inert atmosphere is treated with NaH (60%, 28.8 mg, 0.72 mmol). After 20 min N-(2-chloroethyl)morpholine hydrochloride (37 mg, 0.2 mmol) is added in one portion and the reaction mixture is stirred at 80° C. for 2 h. After cooling to room temperature, the reaction mixture is distributed between water and ethyl acetate. The combined organic phases are dried over anhydrous MgSO₄ and concentrated in vacuo. Flash chromatography (cyclohexane/ethyl acetate) yields 29 mg (34%) of the desired product and 26 mg of recovered starting material.

(d) Trifluoromethanesulfonic acid 8-(naphthalen-1-carbonyl)-5-pentyloxynaphthalen-2-yl ester: A stirred solution of (7-hydroxy-4-pentyloxynaphthalen-1 -yl) naphthalen-1 -yl methanone (1.2 g, 3.13 mmol) in anhydrous pyridine (12 mL) is treated at room temperature with trifluoromethanesulfonic anhydride (0.88 g, 3.13 mmol) and the mixture stirred under nitrogen for 48 h. The solvent is removed under reduced pressure and the residue is diluted with sodium hydrogen carbonate solution and extracted twice with ethyl acetate. The combined organic extracts are washed with water, dried (MgSO₄) and the solvent removed under reduced pressure. The residue is purified by chromatography on silica gel (cyclohexane:ethyl acetate 9:1) to afford the desired product (1.0 g, 67%).

(e) [7-(4-Methylpiperazin-1-yl)4-pentyloxynaphthalen-1-yl] naphthalen-1-yl methanone: A stirred mixture of trifluoromethanesulfonic acid 8-(naphthalen-1-carbonyl)-5-pentyloxynaphthalen-2-yl ester (40 mg, 0.084 mmol), N-methylpiperazine (20 mg, 0.2 mmol), cesium carbonate (38 mg, 0.12 mmol), palladium (II) acetate (2 mg, 10mol %), and BINAP (8 mg, 15mol %) in anhydrous dioxane (0.5 mL) is heated at 80° C. under an argon atmosphere for 30 h. The mixture is cooled to room temperature, diluted with water and extracted with ethyl acetate three times. The combined organic extracts are washed with water, dried (MgSO₄) and the solvent is removed under reduced pressure. The residue is purified by HPLC. All fractions containing product are basified with sodium hydrogen carbonate and extracted with ethyl acetate. The organic extracts are combined, dried (MgSO₄) and evaporated to afford the product as th free base (12 mg, 31%).

EXAMPLE 12

Synthesis of Substitut d Bis-Aryl Ketones

Applicable to Ex. 50, 51, 52, 53, 54, 55, 56, 57, 58, 59, 62, 63, 65, 66, 67, 68, 69, 70, 71, 74, 76, 77, 78.

(a) 8-(Naphthalene-1-carbonyl)-5-pentyloxynaphthalene-2-carbonitrile: A stirred mixture of trifluoromethanesulfonic acid 8-(naphthalen-1-carbonyl)-5-pentyloxynaphthalen-2-yl ester (1.0 g, 2.09 mmol), zinc cyanide (0.294 g, 2.51 mmol) and Pd(PPh₃)₄ (0.121 mg, 0.1 mmol, 5 mol %) in anhydrous DMF (10 mL) is heated under an argon atmosphere at 90° C. for 3 h. The mixture is cooled to room temperature, diluted with water and extracted three times with ethyl acetate, having filtered off insoluble material through Celite filter aid. The combined organic extracts are washed with water, dried (MgSO₄) and the solvent removed under reduced pressure. The residue is purified by chromatography over silica gel (cyclohexane:ethyl acetate 9:1) to afford the desired product (0.53 g, 65%).

(b) Diallyl-(4-bromo-3-fluorophenyl)amine: A stirred mixture of 4-bromo-3-fluoroaniline (17.47 g, 91.9 mmol), allyl bromide (23.72 g, 251.1 mmol) and potassium carbonate (26.7 g, 193.5 mmol) in acetone (200 mL) is refluxed for 24 h. The solvent is removed under reduced pressure and the residue is diluted with water and extracted twice into ethyl acetate. The combined organic extracts are washed with water, dried (MgSO$_4$) and evaporated in vacuo. The residue is purified by chromatography over silica gel (cyclohexane) to afford the desired product (15.27 g, 62%).

(c) Diallyl-(11-oxatricyclo[6.2.1.0_2,7]undeca-2,4,6,9-tetraen-4-yl)amine: A stirred solution of diallyl-(4-bromo-3-fluorophenyl)amine (15.55 g, 57.6 mmol) in anhydrous ether (30 mL) and anhydrous furan (30 mL) is treated with a solution of n-butyllithium in hexanes (36 mL, 57.6 mmol; 1.6 M solution) at −70° C. under an argon atmosphere. After 1 h, the mixture is allowed to warm to room temperature and stirred for a further 4 h. The mixture is quenched with water and extracted three times into ethyl acetate. The combined organic extracts are washed with brine, dried (MgSO$_4$) and the solvent removed under reduced pressure. The residue is purified by chromatography on silica gel (initial eluent cyclohexane, final eluent cyclohexane:ethyl acetate 19:1) to afford the desired product (5.4 g, 39%).

(d) 7-Diallylaminonaphthalen-1-ol: A stirred solution of diallyl-(11-toxatricyclo[6.2.1.0_2,7]undeca-2,4,6,9-tetraen-4-yl)amine (4.48 g, 18.74 mmol) in methanol (45 mL) and concentrated hydrochloric acid (4.5 mL) is refluxed for 5 h. The solvent is removed under reduced pressure and the residue is diluted with water, neutralized with solid sodium hydrogen carbonate and extracted three times with ethyl acetate. The combined extracts are washed with brine, dried (MgSO$_4$) and the solvent removed under reduced pressure. The residue is purified by chromatography on silica gel (initial eluent cyclohexane, final eluent cyclohexane:ethyl acetate 19:1) to afford the desired product (3.67 g, 82%).

(e) Diallyl-(8-pentyloxynaphthalen-2-yl)amine: To a stirred solution of n-pentanol (0.18 g, 2.1 mmol) and triphenylphosphine (0.55 g, 2.1 mmol) in anhydrous THF (10 mL) is added a solution of 7-diallylaminonaphthalen-1-ol (0.5 g, 2.1 mmol) and DIAD (0.45 mL, 2.1 mmol) in anhydrous THF (10 mL). After overnight stirring, the mixture is diluted with brine and extracted three times with ethyl acetate. The combined organic extracts are washed with brine, dried (MgSO$_4$) and evaporated to dryness. The residue is purified by chromatography on silica gel (initial eluent cyclohexane, final eluent cyclohexane:ethyl acetate 98:2) to afford the desired product (0.28 g, 43%).

(f) (6-Diallylamino-4-pentyloxynaphthalen-1-yl) naphthalen-1-yl methanone: To a stirred suspension of anhydrous aluminium chloride (0.24 g, 1.81 mmol) in anhydrous DCM (30 mL) is added naphthoyl chloride (0.205 mL, 1.36 mmol) at 0° C. under a nitrogen atmosphere. After 15 min, a solution of diallyl-(8-pentyloxynaphthalen-2-yl)amine (0.28 g, 0.906 mmol) in anhydrous DCM (5 mL) is added dropwise and the mixture allowed to warm to room temperature and stirred under nitrogen overnight. The mixture is washed with saturated sodium hydrogen carbonate solution (pH 8), and the aqueous phase additionally extracted three times with diethyl ether. The organic phases are combined, washed with water, dried (MgSO$_4$) and the solvent removed under reduced pressure. The residue is purified by chromatography on silica gel (initial eluent cyclohexane, final eluent cyclohexane:ethyl acetate 98:2) to afford the desired product (0.32 g, 75%).

(g) 5-Pentyloxynaphthalen-2-ol: A stirred mixture of naphthalene-1,6-diol (10.0 g, 62.5 mmol), 1-bromopentane (7.75 mL, 62.5 mmol) and sodium hydroxide (2.5 g, 62.5 mmol) in DMSO (100 mL) is heated at 100° C. for 6 h. After cooling to room temperature, the mixture is diluted with water and extracted three times into ethyl acetate. The combined extracts are washed several times with water, dried (MgSO$_4$) and the solvent removed under reduced pressure. The residue is purified by chromatography on silica gel (initial eluent cyclohexane:ethyl acetate 97:3; final eluent cyclohexane:ethyl acetate 90:10) to afford an inseparable mixture of the desired product and the isomeric 6-pentyloxynaphthalen-1-ol (6.18 g, 43%) having first eluted off the doubly-alkylated product, 1,6-bis-(pentyloxy) naphthalene.

(h) Acetic acid 5-pentyloxynaphthalen-2-yl ester: A stirred solution of 5-pentyloxynaphthal n-2-ol/6-pentyloxynaphthalen-1-ol (6.18 g, 26.8 mmol) in DCM (100 mL) in the presence of NEt$_3$ (4.4 mL, 31.6 mmol) is treated dropwise at 0° C. with a solution of acetyl chloride (2.24 mL, 31.5 mmol) in DCM (30 mL). After warming to room temperature and stirring for 3 h, the reaction mixture is washed with brine, dried (MgSO$_4$) and the solvent removed under reduced pressure. The residue is purified by chromatography on silica gel (1.5% ethyl acetate in cyclohexane) to afford the desired product (4.56 g, 56%) and the isomeric acetic acid 6-pentyloxynaphthalen-1-yl ester (1.0 g, 13%).

(i) Acetic acid 8-(naphthalene-1-carbonyl)-5-pentyloxynaphthalen-2-yl ester: To a stirred suspension of anhydrous aluminium chloride (4.42 g, 33.09 mmol) in anhydrous DCM (290 mL) at 0° C. under nitrogen is added dropwise a solution of naphthoyl chloride (3.7 mL, 24.8 mmol) in anhydrous DCM (35 mL). After 15 min, a solution of acetic acid 5-pentyloxynaphthalen-2-yl ester (4.5 g, 16.54 mmol) in anhydrous DCM (70 mL) is added, and the reaction mixture is allowed to warm to room temperature and stir for 20 h. The mixture is washed with saturated sodium hydrogen carbonate solution, the phases separated and the DCM removed under reduced pressure. The residue is taken up in diethyl ether and washed with water, dried (MgSO$_4$) and the solvent removed under reduced pressure. Purification by chromatography on silica gel (1–3% ethyl acetate in cyclohexane) affords the desired product (4.8 g, 68%) and naphthalene-1-carboxylic acid 8-(naphthalene-1-carbonyl)-5-pentyloxynaphthalen-2-yl ester (2.1 g), arising from naphthoyl replacement of the acetyl group.

(k) (7-Hydroxy-4-pentyloxynaphthalen-1-yl) naphthalen-1-yl methanone: A stirred solution of acetic acid 8-(naphthalene-1-carbonyl)-5-pentyloxynaphthalen-2-yl ester (4.8 g, 11.2 mmol) and naphthalene-1-carboxylic acid 8-(naphthalene-1-carbonyl)-5-pentyloxynaphthalen-2-yl ester (2.1 g, 3.9 mmol) in methanol (70 mL) in the presence of 5M NaOH solution (20 mL) is refluxed for 3 h. After cooling to room temperature, the mixture is diluted with water, acidified with acetic acid and extracted three times into ethyl acetate. The combined extracts are washed with water, dried (MgSO$_4$) and the solvent removed under reduced pressure. The residue is recrystallized from ethyl acetate to afford the desired product (3.7 g, 64%) as a bright yellow solid.

EXAMPLE 13

Synthesis of Aryl-Heteroaryl Ketones

Applicable to Ex 45, 92, 93.

(a) Isoquinolin-1 -yl-(4-pentyloxynaphthalen-1 -yl) methanone: To a solution of 1-iodo-4-pentyloxy-naphthalene (419 mg, 1.232 mmol) in THF (8 mL) at −78° C. (acetone/dry ice bath) is added dropwise, NBuli (0.99 mL, 2.5 M in hexanes). A yellow precipitate appears after a few minutes. After stirring for 30 min, a solution of isoquinoline-1-carbonitrile (210 mg, 1.364 mmol) in THF (2 mL) is added, dropwise, by syringe to give a deep red solution. The reaction mixture is withdrawn from the cold bath and allowed to warm to room temperatur over 3 h. A vivid blue solution resulted. Dilute sulfuric acid (2.5 mL, 10% v/v) is then added and the mixture is stirred for 45 min at room temperature. The reaction mixture is then diluted with ethyl acetate and the solution is washed with saturated aqueous sodium hydrogen carbonate until basic (indicator paper), aqueous sodium thiosulfate (×2) and brine; dried over anhydrous $Na_2SO_4$ and concentrated on a rotary evaporator. The crude material is chromatographed on silica gel (gradient elution: cyclohexane/ethyl acetate 9/1 then 5/1 then 2/1) to give the title compound as a bright yellow, viscous oil, (270 mg, 59%).

(b) 4-Pentyloxy-1-naphthalene boronic acid: To a cooled (dry ice/acetone bath) solution of the 1-iodo-4-pentyloxynaphthalene (0.993 g, 2.92 mmol) in THF (10 mL) under dry argon is added n-BuLi (2.5 M in hexanes, 2.4 mL, 6.0 mmol), dropwise, via syringe. The reaction mixture becomes dark yellow and a precipitate appeared. After 0.5 h at the cooling bath temperature, trimethylborate (0.66 mL, 5.8 mmol) is added, dropwise, via syringe. The reaction flask is removed from the cold bath and the yellow colour faded to colourless after a few minutes. After 1.5 h, sulfuric acid (20% v/v, 3 mL) is added and the resulting suspension is distributed between ethyl acetate and water. The organic layer is washed with aqueous sodium thiosulfate (×2) and brine, dried (anhydrous $Na_2SO_4$) and evaporated on a rotary evaporator. The residue is taken up in the minimum volume of DCM and applied to a silica gel column, which is eluted with cyclohexane/ethyl acetate (1/1) to give the boronic acid (267 mg, 35%).

(c) (4-Pentyloxynaphthalen-1-yl)quinolin-8-yl methanone: To a three-necked, flame-dried flask outfitted with a gas inlet and septum is added 8-hydroxyquinoline trifluoromethansulfonate (122.8 mg, 0.442 mmol), 4-pentyloxy-1-naphthalene boronic acid (124.5 mg, 0.482 mmol), anhydrous potassium carbonate (199.7 mg, 1.447 mmol) $PdCl_2dppf.CH_2Cl_2$ complex (10.5 mg, 0.0128 mmol, Avocado) and sodium iodide (150 mg). The reaction flask is evacuated (house vacuum) and flushed with carbon monoxide from a balloon (3 cycles). Anisole 3 mL is added by syringe and the stirred orange reaction mixture is placed in a preheated oil bath at 80° C. After 3 h, additional anisole (1 mL) is added and the reaction mixture is left to stir at 80° C. overnight. The reaction mixture, which becomes black, is allowed to cool to room temperature and diluted with ethyl acetate and water. The organic layer is washed with brine (×2), dried over anhydrous $Na_2SO_4$, and concentrated on a rotary evaporator. The crude material is chromatographed on silica gel (cyclohexane/ethyl acetate 5/1) to provide the title compound as a green oil (52 mg, 32%).

EXAMPLE 14

Synthesis f Benzimidaz l nes, Benzimidaz les and Benzotriaz les

Applicable to Ex: 150, 151, 152, 153, 154, 155, 156, 157, 158, 159, 160, 161, 162.

(a) N-(2-Pentyloxy-phenyl)-acetamide: 2-Acetamidophenol (5 g, 33.09 mmol) is dissolved in dry DMF (35 mL) at room temperature. Cesium carbonate (17.25 g, 52.53 mmol) is added, followed by 1-bromopentane (6.15 mL, 49.61 mmol) and the mixture is stirred at 60° C. for 16 h. The reaction mixture is cooled to room temperature, diluted with water (400 mL) and extracted with ethyl acetate (3×100 mL). The ethyl acetate extracts are combined, washed with saturated brine, dried ($MgSO_4$), filtered and concentrated under reduced pressure to give sufficiently pure product (6.02 g, 82%).

(b) N-[5-(Naphthalene-1-carbonyl)-2-pentyloxy-phenyl]-acetamide: In a dried flask purged with dry nitrogen, aluminium chloride (5.45 g, 40.86 mmol) is suspended in dry 1,2-dichloroethane (50 mL). The suspension is cooled with an ice-water bath before a solution of 1-naphthoyl chloride (4.51 mL, 29.96 mmol) in dry 1,2-dichloroethane (10 mL) is added in one portion. After 10 minutes N-(2-pentyloxy-phenyl)-acetamide (6.02 g, 27.24 mmol) is added and the reaction mixture is allowed to warm to room temperature overnight. The mixture is poured onto a mixture of ice-water and 5M aqueous sodium hydroxide (sufficient quantity to make the aqueous layer basic), stirred for 15 minutes and extracted with ethyl acetate (4×100 mL). The organic extracts are combined and washed with saturated brine (100 mL), dried ($MgSO_4$), filtered and concentrated under reduced pressure. The crude product is purified by chromatography on silica gel using a Biotage apparatus (90 g column; Dyax Corp.) and cyclohexane:ethyl acetate (2:1) as eluant to give the product as a thick oil (3.68 g, 36%). A further 5.64 g of slightly impure material is also obtained which is sufficiently pure to be used in subsequent reactions.

(c) (3-Amino-4-pentyloxy-phenyl)-naphthalen-1-yl-methanone: N-[5-(Naphthalene-1-carbonyl)-2-pentyloxy-phenyl]-acetamide (1.78 g, 4.75 mmol) is dissolved in methanol (20 mL) at room temperature. Aqueous hydrochloric acid (10M, 20 mL) is added and the mixture is heated at reflux for 1 h. The reaction mixture is evaporated to dryness under reduced pressure, partitioned between saturated aqueous sodium bicarbonate and ethyl acetate and extracted with further portions of ethyl acetate (3×100 mL). The ethyl acetate extracts are combined, washed with saturated brine, dried ($MgSO_4$), filtered and concentrated under reduced pressure to give the crude product as a non-viscous brown oil. This is purified on silica gel using Biotage (90 g column) and cyclohexane:ethyl acetate (4:1) as eluant to give pure product (0.97 g, 61%).

(d) 3-[5-(Naphthalene-1-carbonyl)-2-pentyloxy-phenyl]-1-methoxyurea: Di-tert-butyldicarbonate (1.833 g, 8.4 mmol) is dissolved in dry DCM (20 mL) at room temperature and DMAP (0.733 g, 6 mmol) is added. The reaction mixture is stirred at room temperature for 5 minutes before a solution of (3-amino-4-pentyloxy-ph nyl)-naphthalen-1-yl-methanone (2.0 g, 6 mmol in dry DCM (10 mL) was added. The mixture is stirred at room temperature for 30 minutes. DIEA (1.045 mL, 6 mmol) and methoxylamine hydrochloride (0.501 g, 6 mmol) are added and the reaction is stirred at room temperature for 4 h. The reaction mixture is treated with water (200 mL) and extracted with DCM (3×75 mL). The DCM extracts are combined, washed with saturated brine, dried ($MgSO_4$), filtered and concentrated under reduced pressure to give the crude product. This is chromatographed on silica gel using Biotage (40 g cartridge) and cyclohexane:ethyl acetate (4:1) as eluant to give 1.25 g of the expected product along with 0.66 g of a product containing an additional t-butyloxycarbonyl group. This is taken up in DCM-trifluoroacetic acid (1:1, 6 mL) and stirred at room temperature for 2 h. Volatiles are removed under reduced pressure and the residue partitioned between DCM (20 mL) and saturated aqueous sodium bicarbonate (50 mL). This mixture is extracted with further DCM (3×50 mL) and the DCM extracts are combined, washed with saturated brine, dried (MgSO$_4$), filtered and concentrated under reduced pressure to give the expected product (1.88 g, 77%).

(e) 1-Methoxy-7-(naphthalene-1-carbonyl)-4-pentyloxy-1,3-dihydro-benzoimidazol-2-one: 3-[5-(Naphthalene-1-carbonyl)-2-pentyloxyphenyl]-1-methoxyurea (650 mg, 1.6 mmol) is dissolved in dry DCM (60 mL) under a nitrogen atmosphere, the solution is cooled to 0° C. and bis(trifluoroacetoxy)iodobenzene (757 mg, 1.76 mmol) is added portionwise. The reaction mixture is allowed to warm to room temperature over 1.5 h before water (200 mL) is added. The mixture is extracted with DCM (3×100 mL) and the DCM extracts are combined, washed with saturated brine (100 mL), dried (MgSO$_4$), filtered and concentrated under reduced pressure to give the crude product as a brown oil. This is chromatographed on silica gel using Biotage (40 g cartridge) and cyclohexane:ethyl acetate (3:1) as eluant to give the expected product (0.34 g, 53%).

(f) 4-(Naphthalene-1-carbonyl)-7-pentyloxy-1,3-dihydro-benzoimidazol-2-one triuoroacetate: 1Methoxy-7-naphthalene-1-carbonyl)-4-pentyloxy-1,3-dihydro-benzoimidazol-2-one (800 mg, 1.98 mmol) is dissolved in glacial acetic acid (10 mL) and zinc powder (5.18 g, 79.22 mmol) is added. The mixture is heated at 50° C. and sonicated for 2 h, cooled to room temperature and filtered through a pad of Celite filter aid. The Celite pad is washed with ethyl acetate and then the volatiles are removed under reduced pressure to give the product as an orange oil. Purification by chromatography on silica gel using Biotage (40 g cartridge) and DCM:methanol (20:1) as eluant gave the desired product (0.67 g, 90%).

(g) (2-Chloro-7-pentyloxy-3H-benzoimidazol-4-yl)-naphthalen-1-yl-methanone: 4-(Naphthalene-1-carbonyl)-7-pentyloxy-1,3-dihydro-benzoimidazol-2-one (500 mg, 1.34 mmol) is dissolved in phosphorus oxychloride (10 mL) and refluxed (oil bath temperature 105° C.) for 30 minutes. The reaction mixture is cooled to room temperature, poured onto ice-cold 2M aqueous sodium hydroxide to neutralise the mixture and extracted with DCM (3×100 mL). The combined DCM extracts are washed with saturated aqueous sodium bicarbonate (3×50 mL), dried (MgSO$_4$), filtered and concentrated under reduced pressure to give the crude product (500 mg, 95%) which is used directly without further purification.

(h) (2-Benzylamino-7-pentyloxy-3H-benzoimidazol-4-yl)-naphthalen-1-yl-methanone trifluoroacetate: (2-Chloro-7-pentyloxy-3H-benzoimidazol-4-yl)-naphthalen-1-yl-methanone (55 mg, 0.14 mmol) and benzylamine (1 mL) are heated together neat at 135° C. for 4 h and then cooled to room temperature. The crude reaction mixture is poured onto water (10 mL), 10% aqueous hydrochloric acid (10 mL) is added and the mixture is extracted with DCM (4×20 mL). The DCM extracts are combined, washed with saturated brine (50 mL), dried (MgSO$_4$), filtered and concentrated under reduced pressure to give the crude product which is purified by preparative reverse phase hplc (Dynamax 300 Å C18 column; 20% acetonitrile in water (+0.1% trifluoroacetic acid) to 100% acetonitrile over 30 minutes) to give 15.4 mg of the desired product.

(i) Acetic acid 2,3-bis-acetylamino-phenyl ester 2,3-Diaminophenol (3.226 g, 25.99 mmol) is dissolved in acetic anhydride (50 mL) and the mixture heated at 70° C. for 4 h. The mixture is cooled to room temperature and allowed to stand for 48 h. The precipitate formed is collected by filtration, washed with ethyl acetate and dried under vacuum to give a white solid (3.99 g, 61%).

(k) N-(2-Acetylamino-6-hydroxy-phenyl)-acetamide (CAS Reg, No. 116345-46-1): Acetic acid 2,3-bis-acetylamino-phenyl ester (3.99 g, 15.96 mmol) is dissolved in dry methanol (50 mL) under nitrogen atmosphere. A solution of sodium methoxide (from sodium metal (0.404 g, 17.56 mmol) in dry methanol (10 mL)) is added and the mixture is stirred at room temperature for 16 h. The solvent is removed under reduced pressure and water is added to the residue, which is then acidified to pH1 with 1M hydrochloric acid. The aqueous layer is concentrated under reduced pressure to precipitate the product which is recovered by filtration and dried under vacuum to give a white solid (1.96 g, 59%).

(l) N-(2-Acetylamino-6-pentyloxy-phenyl)-acetamide: N-(2-Acetylamino-6-hydroxy-phenyl)acetamide (1.46 g, 7.02 mmol) is dissolved in dry DMF (50 mL) at room temperature. Cesium carbonate (2.97 g, 9.13 mmol) and 1-bromopentane (1.04 mL, 8.42 mmol) are added and the mixture is heated at 60° C. for 20 h and then stirred at room temperature for 4 days. Water (800 mL) is added and th solution is xtracted with DCM (4×100 mL). The DCM extracts are combined, washed with saturated brine (50 mL), dried (MgSO$_4$), filtered and concentrated under reduced pressure to give the crude product, 1.95 g. This is recrystallized from ethyl acetate/cyclohexane to give pure material (0.9 g, 46%).

(m) N-(2-Acetylamino-3-iodo-6-pentyloxy-phenyl)-acetamide: To a solution of N-(2-acetylamino-6-pentyloxy-phenyl)-acetamide (0.9 g, 3.24 mmol) and periodic acid hydrate (129 mg, 0.57 mmol) in acetic acid-water-sulfuric acid (100:20:3; 10 mL) is added iodine (332 mg, 1.31 mmol). The mixture is stirred at room temperature for 16 h, diluted with 10% aqueous sodium thiosulfate (100 mL) and then extracted with DCM (1×100 mL), ethyl acetate (1×100 mL) and diethyl ether (1×100 mL). The organic extracts are combined, washed with saturated brine (50 mL), dried (MgSO$_4$), filtered and concentrated under reduced pressure to give the crude product which is recrystallized from ethyl acetate to give pure material (550 mg, 42%).

(n) 7-Iodo-2-methyl-4-pentyloxy-1H-benzoimidazole: N-(2-Acetylamino-3-iodo-6-pentyloxy-phenyl)-acetamide (100 mg, 0.248 mmol) is added to a solution of potassium hydroxide (139 mg, 2.48 mmol) in ethanol (5 mL) and water (1 mL). The mixture is heated at reflux for 3 h, left to stand for 2 days and then heated at reflux for a further 6 h before standing at room temperature for 8 days. Volatiles are removed under reduced pressure and the residue partitioned between ethyl acetate (10 mL) and water (10 mL) and extracted with further aliquots of ethyl acetate (3×10 mL). The ethyl acetate extracts are combined, washed with saturated brine (50 mL), dried (MgSO$_4$), filtered and concentrated under reduced pressure to give the crude product. Purification by chromatography on silica gel (Biotage, 40 g cartridge) using cyclohexane:ethyl acetate (3:1) as eluant gave the title compound (35.5 mg, 42%).

(o) (2-Methyl-7-pentyloxy-3H-benzoimidazol-4-yl)-naphthalen-1-yl-methanone: 7-iodo-2-methyl-4-pentyloxy-1H-benzoimidazole (35 mg, 0.102 mmol), anhydrous potassium carbonate (42 mg, 0.306 mmol), 1-naphthaleneboronic acid (19 mg, 0.112 mmol), and PdCl$_2$dppf CH$_2$Cl$_2$ (3 mg, 0.003 mmol) are mixed in anhydrous anisole (5 mL) and placed under an atmosphere of carbon monoxide. The mixture is heated at 80° C. for 20 h, cooled to room temperature and diluted with water (10 mL). The mixture is extracted with DCM (2×10 mL) and ethyl acetate (3×10 mL) and the organic extracts are combined, washed with saturated brine (50 mL), dried (MgSO$_4$), filtered and concentrated under reduced pressure to give the crude product. This is purified by preparative reverse phase hplc (Dynamax 300 Å C18 column; 20% acetonitrile in water (+0.1% trifluoroacetic acid) to 100% acetonitrile over 30 minutes) to give 12.7 mg of the desired product.

(p) N[2-(Acetyloxy)-6-nitrophenyl]-acetamide (CAS Reg. No. 69194-51-0): 2-Amino-3-nitrophenol (3 g, 19.46 mmol) is dissolved in acetic anhydride (20 mL) and the mixture heated at 50° C. for 16 h. After cooling to room temperature, water (400 mL) is added and the mixture is extracted with DCM (3×100 mL). The DCM extracts are combined, washed with saturated brine (50 mL), dried ($MgSO_4$), filtered and concentrated under reduced pressure to give the pure title compound (4.14 g, 89%).

(q) N-(2-hydroxy-6-nitrophenyl)-acetamide (CAS Reg. No. 59820-29-0): N-[2-(Acetyloxy)-6-nitrophenyl]-acetamide (4.13 g, 17.35 mmol) is dissolved in dry methanol (20 mL) and a fresh solution of sodium methoxide (from sodium (0.6 g, 26.03 mmol) in dry methanol (15 mL)) is added. The reaction mixture is stirred at 50° C. for 2 h, cooled to room temperature and the methanol removed under reduced pressure. Water (100 mL) is added, the pH adjusted to pH1 using 2M aqueous hydrochloric acid and the solution extracted with ethyl acetate (3×100 mL). The ethyl acetate extracts are combined, washed with saturated brine (50 mL), dried ($MgSO_4$), filtered and left to stand at room temperature for 7 days. The crystals that formed are collected by filtration and dried to give pure product (1.5 g, 44%). The mother liquor is concentrated under reduced pressure to give further crude product (2.3 g), which is pure enough for use in subsequent reactions.

(r) N-(2-Nitro-6-pentyloxy-phenyl)-acetamide: N-(2-hydroxy-6-nitrophenyl)-acetamide (3.8 g, 19.39 mmol) is dissolved in dry DMF (25 mL). Cesium carbonate (8.83 g, 27.1 mmol) and 1-bromopentane (23.26 mmol) are added and the mixture is stirred at 80° C. for 2 h. After cooling to room temperature water (400 mL) is added and the mixture is extracted with ethyl acetate (3×100 mL). The ethyl acetate extracts are combined, washed with saturated brine (50 mL), dried ($MgSO_4$), filtered and concentrated under reduced pressure to give the crude product. This is recrystallised from ethyl acetate/n-hexane at 4° C. to give the title compound (1.74 g, 34%). The mother liquor is concentrated under reduced pressure to give further crude product which is purified by chromatography on silica gel (Biotage, 40 g cartridge) using DCM:methanol (50:1) as eluant. This gives a further 0.79 g (15%) of the title compound and 0.31 g (7%) of the de-acetylated product, 2-nitro-6-pentyloxy-phenylamine.

(s) 2-Nitro-6-pentyloxy-phenylamine: N-(2-Nitro-6-pentyloxy-phenyl)-acetamide (1.74 g, 6.53 mmol) is dissolved in methanol (50 mL) and 10 M hydrochloric acid (25 mL) is added. The mixture is heated at reflux for 4 h, cooled to room temperature and the methanol removed under reduced pressure. The residue is adjusted to pH12 using 5M aqueous sodium hydroxide and extracted with ethyl acetate (3×100 mL). The ethyl acetate extracts are combined, washed with saturated brine (50 mL), dried ($MgSO_4$), filtered and concentrated under reduced pressure to give the pure product (1.46 g, 100%).

(t) 3-Pentyloxy-benzene-1,2-diamine: 2-Nitro-6-pentyloxyphenylamine (1.46 g, 6.52 mmol) is dissolved in ethyl acetate (20 mL) and the flask is purged with nitrogen. 10% Palladium on activated carbon (50 mg) is added and the reaction is evacuated and purged three times with hydrogen. The mixture is stirred for 24 h under a hydrogen atmosphere by means of a balloon filled with hydrogen gas. Methanol (20 mL) is added to encourage solubilisation and the reaction stirred for a further 2 h at room temperature. The reaction is purged with nitrogen, filtered through a pad of Celite filter aid and concentrated under reduced pressure to give a white solid that could be recrystallized from ethyl acetate/methanol to give the title compound (1.007 g, 80%).

(u) 7-Pentyloxy-1H-benzoimidazole: 3-Pentyloxy-benzene-1,2-diamine (200 mg, 1.03 mmol) and trimethylorthoformate (2 mL) are mixed together in a pyrex tube and subjected to microwave irradiation at 100W for 30 seconds in a Labwell MW10 laboratory microwave instrument. Removal of volatiles under reduced pressure gave the pure product as a cream solid (217 mg, 100%).

(v) 4-Iodo-7-pentyloxy-1H-benzoimidazole: 7-Pentyloxy-1H-benzoimidazole (100 mg, 0.49 mmol) is dissolved in acetic acid-water-sulfuric acid (100:20:3; 5 mL) and periodic acid hydrate (22 mg, 0.098 mmol) is added, followed by iodine (50 mg, 0.196 mmol). The reaction mixture is stirred at room temperature for 4 h and at 80° C. for 16 h. After cooling to room temperature, 10% aqueous sodium thiosulfate (100 mL) is added and the mixture is extracted with ethyl acetate (3×25 mL). The ethyl acetate extracts are combined, washed with saturated brine (50 mL), dried ($MgSO_4$), filtered and concentrated under reduced pressure to give the crude product. This is purified by chromatography on silica gel (Biotage, 40 g cartridge) to give the title compound (65 mg, 40%).

(w) Naphthalen-1-yl-(7-pentyloxy-3H-benzoimidazol-4-yl)-methanone: 4-Iodo-7-pentyloxy-1H-benzoimidazole (65 mg, 0.197 mmol), anhydrous potassium carbonate (82 mg, 0.591 mmol), 1-naphthaleneboronic acid (37 mg, 0.217 mmol), and $PdCl_2dppf\ CH_2Cl_2$ (9 mg, 0.011 mmol) are mixed in anhydrous anisole (5 mL) and placed under an atmosphere of carbon monoxide. The mixture is heated at 80° C. for 18 h, cooled to room temperature and diluted with water (10 mL). The mixture is extracted with DCM (2×10 mL) and ethyl acetate (3×10 mL) and the organic extracts are combined, washed with saturated brine (50 mL), dried ($MgSO_4$), filtered and concentrated under reduced pressure to give the crude product. This is purified by chromatography on silica gel (Biotage, 40 g cartridge) using cyclohexane:ethyl acetate (3:1) as eluant to give the title compound (15 mg, 21%).

(x) 7-Pentyloxy-1H-benzotriazole: 3-Pentyloxy-benzene-1,2-diamine (100 mg, 0.516 mmol) is dissolved in glacial acetic acid (5 mL) and water (5 mL). The reaction mixture is cooled to 0° C. and a cold solution of sodium nitrite (39 mg, 0.568 mmol) in water (5 mL) is added in one portion. The reaction mixture is allowed to warm slowly to room temperature overnight, diluted with water (20 mL) and extracted with DCM (3×50 mL). The DCM extracts are combined, washed with saturated brine (50 mL), dried ($MgSO_4$), filtered and concentrated under reduced pressure to give the title compound (90 mg, 85%), which could be used without further purification.

(y) 4-Iodo-7-pentyloxy-1H-benzotriazole: 7-Pentyloxy-1H-benzotriazole (90 mg, 0.439 mmol) is dissolved in acetic acid-water-sulfuric acid (100:20:3; 10 mL) and periodic acid hydrate (20 mg, 0.088 mmol) is added, followed by iodine (45 mg, 0.176 mmol). The reaction mixture is stirred at 80° C. for 5 h. After cooling to room temperature, 10% aqueous sodium thiosulfate (10 mL) is added and the mixture is extracted with ethyl acetate (3×25 mL). The ethyl acetate extracts are combined, washed with saturated brine (50 mL), dried ($MgSO_4$), filtered and concentrated under reduced pressure to give the crude product. This is purified by chromatography on silica gel (Biotage, 40 g cartridge) to give the title compound (67 mg, 46%) along with 124 mg of mainly di-iodinated material (4,6-diiodo-7-pentyloxy-1H-benzotriazole) contaminated with the title compound.

(z) Naphthalen-1-yl-(7-pentyloxy-3H-benzotriazol-4yl)-methanone: 4-iodo-7-pentyloxy-1H-benzotriazole (67 mg, 0.202 mmol), anhydrous potassium carbonate (84 mg, 0.607 mmol), 1-naphthaleneboronic acid (38 mg, 0.223 mmol), and PdCl$_2$dppf.CH$_2$Cl$_2$ (17 mg, 0.02 mmol) are mixed in anhydrous anisole (5 mL) and placed under an atmosphere of carbon monoxide. The mixture is heated at 80° C. for 20 h, cooled to room temperature and diluted with water (20 mL). The mixture is extracted with DCM (2×10 mL) and ethyl acetate (3×10 mL) and the organic extracts are combined, washed with saturated brine (50 mL), dried (MgSO$_4$), filtered and concentrated under reduced pressure to give the crude product. This is purified by chromatography on silica gel (Biotage, 40 g cartridge) using cyclohexane:ethyl acetate (4:1) as eluant to give the title compound (44 mg, 61%).

Characterising Data

Compounds of the above tables are found to exhibit the following melting point data, HPLC retention data [min] and/or ion mass:

| Ex. | melting point [°C.] | Ion mass (ion) |
|---|---|---|
| 2 | 118–119 | 372 M+ |
| 3 | 88–91 | 388 M+ |
| 4 | 143–144 | 404 M+ |
| 5 | | 418 [M + H]+ |
| 6 | | 404 M+ |
| 7 | 93–95 | 369 [M + H]+ |
| 8 | 118–120 | 385 [M + H]+ |
| 9 | 158–160 | 396 [M + H]+ |
| 10 | 207–210 | 412 [M + H]+ |
| 11 | 78–80 | 410 [M + H]+ |
| 12 | | 378 [M − H]− |
| 13 | | 454 [M − H]− |
| 14 | | 384 M+ |
| 15 | | 400 M+ |
| 16 | | 442 [M + Na]+ |
| 17 | 58–63 | 382 [M − H]− |
| 18 | 70–71 | 399 [M + H]+ |
| 19 | 107–108 | 437 [M + Na]+ |
| 20 | | 407 M+ |
| 21 | | 405 M+ |
| 22 | | 439 M+ |
| 23 | | 494 [M + H]+ |
| 24 | | 355 M+ |
| 25 | 127–130 | 418 [M − H]− |
| 26 | | 369 M+ |
| 27 | 95–100 | 383 [M − H]− |
| 28 | | 335 M+ |
| 29 | | 370 M+ |
| 30 | | 367 M+ |
| 31 | 106–111 | 366 M+ |
| 32 | | 388 M+ |
| 33 | | 374 M+ |
| 34 | | 369 M+ |
| 35 | | 426 M+ |
| 36 | 92–94 | 385 M+ |
| 37 | 126–130 | 385 M+ |
| 38 | 136–138 | 385 M+ |
| 39 | | 398 M+ |
| 40 | | 799 [2M + Na]+ |
| 41 | | 419 [M + H]+ |
| 42 | | 405 M+ |
| 43 | | 377 M+ |
| 44 | | 361 M+ |
| 45 | | 398 [M + H]+ |
| 46 | 55–60 | 389 M+ |
| 47 | | 451.2 [M + Na]+ |

| Ex. | RT* [min] | Ion mass (ion) |
|---|---|---|
| 45 | 6.9, C | 398 [M + H]+ |
| 47 | 3.4, C | 451.2 [M + Na]+ |
| 48 | 8.4, A | 371.4 [M + H]+ |
| 49 | 10.7, C | 525.3 [M + H]+ |
| 50 | 11.1, C | 464.4 [M + H]+ |
| 51 | 7.4, A | 424.3 [M + H]+ |
| 52 | 8.4, A | 539.2 [M + H]+ |
| 53 | 9.4, C | 427.2 [M + H]+ |
| 54 | 9.3, C | 385.1 [M + H]+ |
| 55 | 7.2, A | 457.2 [M + H]+ |
| 56 | 9.1, C | 443.2 [M + H]+ |
| 57 | 5.6, A | 384.1 [M + H]+ |
| 58 | 7.2, A | 499.3 [M + H]+ |
| 59 | 8.8, A | 481.3 [M + H]+ |
| 60 | 5.1, A | 467.3 [M + H]+ |
| 61 | 5.1, A | 453.3 [M + H]+ |
| 62 | 6.1, A | 384.1 [M + H]+ |
| 63 | 6.7, A | 412.2 [M + H]+ |
| 64 | 7.1, A | 412.2 [M + H]+ |
| 65 | 7.4, A | 394.1 [M + H]+ |
| 66 | 6.6, A | 437.3 [M + H]+ |
| 67 | 7.4, A | 399 [M + H]+ |
| 68 | 6.8, A | 451.3 [M + H]+ |
| 69 | 7.4, A | 451.3 [M + H]+ |
| 70 | 7.6, A | 412.3 [M + H]+ |
| 71 | 8.4, A | 413.3 [M + H]+ |
| 72 | 10.0, C | 427.3 [M + H]+ |
| 73 | 8.7, C | 413.1 [M + H]+ |
| 74 | 8.9, A | 451.3 [M + H]+ |
| 75 | 8.0, C | 470.4 [M + H]+ |
| 76 | 10.3, C | 445 [M + H]+ |
| 77 | 6.9, A; 9.4, C | 403 [M + H]+ |
| 78 | 7.6, A | 450 [M − H]− |
| 79 | | 389 M+ |
| 80 | | 373 M+ |
| 81 | 10.8, A | 369.2 [M + H]+ |
| 82 | 8.1, A | 414.3 [M + H]+ |
| 83 | 9.1, A | 384.3 [M + H]+ |
| 84 | 7.5, A | 412 [M + H]+ |
| 85 | 7.7, A | 399.3 [M + H]+ |
| 86 | 7.6, A | 414.2 [M + H]+ |
| 87 | 8.4, C | 384.2 [M + H]+ |
| 88 | 8.0, C | 370.3 [M + H]+ |
| 89 | 8.7, C | 370.4 [M + H]+ |
| 90 | 9.8, C | 370.3 [M + H]+ |
| 91 | 7.1, A | 412.2 [M + H]+ |
| 92 | 6.5, A | 370.0 [M + H]+ |
| 93 | 9.1, C | 370.2 [M + H]+ |
| 94 | 7.8, A | 386 M+ |
| 95 | 7.5, A | 393 M+ |
| 96 | 6.7, A; 9.2, C | 436 [M + H]+ |
| 97 | 9.0, C | 437 [M + H]+ |
| 98 | 7.1, A | 455 [M + H]+ |
| 99 | 11.9, C | 455 [M + H]+ |
| 100 | 7.2, C | 498 [M + H]+ |
| 101 | 6.7, A | 462.2 [M + H]+ |
| 102 | 6.7, A | 462.3 [M + H]+ |
| 103 | 7.3, A; 10.1, C | 435 [M + H]+ |
| 104 | 6.9, C | 435 [M + H]+ |
| 105 | 6.8, A | 413 [M + H]+ |
| 106 | 6.3, A | 412 [M + H]+ |
| 107 | 6.9, A; 3.4, C | 385 [M + H]+ |
| 108 | 7.5, A; 6.8, C | 427 [M + H]+ |
| 109 | 5.5, A | 411 M+ |
| 110 | 9.6, A | 354 M+ |
| 111 | 9.1, B | 341 [M + H]+ |
| 112 | 5.9, B | 410.3 [M + H]+ |
| 113 | 9.5, B | 432 M+ |
| 114 | 9.4, B | 403.2 [M + H]+ |
| 115 | 9.5, B | 448.2 [M + H]+ |
| 116 | 7.1, B | 446 [M + H]+ |
| 117 | 6.7, B | 418 [M + H]+ |
| 118 | 5.7, B | 426 [M + H]+ |
| 119 | 9.6, B | |
| 120 | 9.3, B | 354.3 [M + H]+ |
| 121 | 9.5, B | 427.2 [M + H]+ |
| 122 | 9.2, B | 413.1 [M + H]+ |
| 123 | 7.2, B | 418 [M + H]+ |

-continued

| | | |
|---|---|---|
| 124 | 10.6, A | 446 [M + H]+ |
| 125 | 6.1, A | 424.2 [M + H]+ |
| 126 | 6.5, A | 467 [M + H]+ |
| 127 | 9.7, B | 368 [M + H]+ |
| 128 | 7.4, B | 357 [M + H]+ |
| 129 | 7.8, B | 385.4 [M + H]+ |
| 130 | 7.4, B | 371.4 [M + H]+ |
| 131 | 8.4, A | 383 [M + H]+ |
| 132 | 8.7, A | 397 [M + H]+ |
| 133 | 9.8, B | 368.4 [M + H]+ |
| 134 | 8.0, A | 382.3 [M + H]+ |
| 135 | | 371.2 [M + H]+ |
| 136 | 8.4, C | 371.3 [M + H]+ |
| 137 | 6.7, A | 395.2 [M + H]+ |
| 138 | 7.0, A | 409.1 [M + H]+ |
| 139 | 7.5, A | 423.1 [M + H]+ |
| 140 | 8.0, A; 10.8, C | 383.2 [M + H]+ |
| 141 | 7.2, A; 7.8, C | 382.3 [M + H]+ |
| 142 | 7.3, A; 10.0, C | 367.2 [M + H]+ |
| 143 | 7.3, A; 10.0, C | 367.2 [M + H]+ |
| 144 | 9.5, C | 305.2 [M + H]+ |
| 145 | 9.2, C | 351.3 [M + H]+ |
| 146 | 8.7, A | 365.4 [M + H]+ |
| 147 | 9.1, C | 305.2 [M + H]+ |
| 148 | 4.5, C | 362.3 [M + H]+ |
| 149 | 5.9, B | 307 [M + H]+ |
| 150 | 5.3, A; 5.9, C | 373.2 [M + H]+ |
| 151 | 5.8, A; 5.8, C | 359.3 [M + H]+ |
| 152 | 6.1, A; 8.0, C | 360.3 [M + H]+ |
| 153 | 7.6, A; 8.0, C | 407.2 [M + H]+ |
| 154 | 6.8, A; 7.3, C | 375.2 [M + H]+ |
| 155 | 6.3, A; 7.1, C | 482.3 [M + H + H2O]+ |
| 156 | 7.9, A; 8.7, C | 470.6 [M + H]+ |
| 157 | 3.2, A; 3.6, C | 547.3 [M + H + H2O + MeCN]+ |
| 158 | 7.9, A; 8.8, C | 489.3 [M + H + H2O + MeCN]+ |
| 159 | 4.8, A; 5.3, C | 457.4 [M + H]+ |
| 160 | 5.4, A; 5.9, C | 436.3 [M + H + H2O]+ |
| 161 | 5.2, A; 5.8, C | 480.2 [M + H + H2O]+ |
| 162 | 7.6, A; 7.6, C | 405.3 [M + H]+ |
| 163 | 4.6, A; 5.9 C | 451.5 [M + H]+ |

*HPLC conditions A: Kingsorb 3 micron C18 column, 30 × 4.6 mm, Gradient elution 10 to 100% acetonitrile in water (+0.1% trifluoroacetic acid) over 10 min.
HPLC conditions B: Kingsorb 3.5 micron C18 column, 50 × 4.6 mm, Gradient elution 10 to 100% acetonitrile in water (+0.1% trifluoroacetic acid) over 10 min.
HPLC conditions C: Kingsorb 3 micron C18 column, 30 × 4.6 mm, Gradient elution 10 to 100% acetonitrile in water (+0.1% trifluoroacetic acid) over 12 min.

The invention claimed is:

1. A compound of formula I

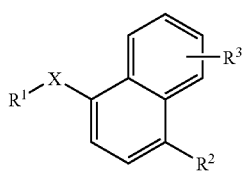

(I)

wherein
X is —S—, —S(O)—, —S(O)$_2$—, —S(O)$_2$NH—, —P(O)(OCH$_3$)—, —P(O)(OH)—, —NH—, —N(CH$_3$)—, —NHC(O)NH—, —C(O)—, —C(O)O—, —NHC(O)—, —CH(OH)—, —CH=N—, —CH=CH—, —CH$_2$NH— or —C(=NH)—;

$R^1$ is aryl or heteroaryl;
$R^2$ is hydrogen, $OR^4$ or $NR^5R^6$;
$R^4$ is $C_1$–$C_8$alkyl or $C_2$–$C_8$alkenyl;
$R^5$ and $R^6$ independently are hydrogen, $C_1$–$C_8$alkyl or C(O)$C_1$–$C_8$alkyl; and
$R^3$ is hydrogen, cyano, heteroaryl, heterocycloalkyl, C(O)$R^7$, $OR^8$ or $NR^9R^{10}$;
$R^7$ is OH, $C_1$–$C_4$alkoxy, $NH_2$, $NHCH_2C(O)OH$ or aryl;
$R^8$ is hydrogen, $C_1$–$C_8$alkyl, C(O)$C_1$–$C_4$alkyl or C(O)-aryl; and
$R^9$ and $R^{10}$ independently are hydrogen, $C_1$–$C_8$alkyl or $C_2$–$C_4$alkenyl;
with the proviso that when X is —C(O)— and $R^2$ and $R^3$ are hydrogen or $R^2$ is H and $R^3$ is 4-methoxy, $R^1$ is not 1-naphthyl nor 4-methoxy-1-naphtyl nor phenyl;
in free base or acid addition salt form.

2. A compound of claim 1 wherein X=—C(O)—, $R^1$=naphthyl, $R^2$=—O—(CH$_2$)$_4$CH$_3$ and $R^3$=—H.

3. A process for the production of a compound of formula I according to claim 1, comprising the steps of
(a) reacting a compound of formula II

$R^1$–$R^{13}$ (II)

wherein $R^1$ is as defined as in claim 1 and $R^{13}$ is —OH, —SH, —I, —Cl, 1,8-bis(dimethylamino)naphthalene-, —COOH, —NH$_2$, —H, -carbonitrile, —O-trifluoromethansulfonyl, —C(O)Cl, with a compound of formula III

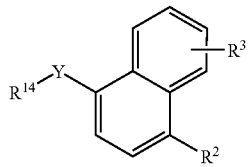

(III)

wherein $R^2$ and $R^3$ are as defined as in claim 1, Y is —O—, —S(O)$_2$O—, —P(O)(OCH$_3$)—, a single bond, —C(O)O—, —C(O)—, —B(OH)$_2$, and $R^{14}$ is e.g. hydrogen, —I, —Cl, thus obtaining a compound of formula Ia

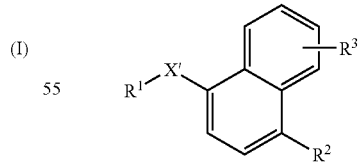

(Ia)

wherein $R^1$, $R^2$ and $R^3$ are as defined as in claim 1, and X' is —CO—, —S—, —P(O)(OCH$_3$)—, —NH—, —S(O)$_2$- (obtainable via process (a) when binding partner at $R^1$=N), —S(O)$_2$NH—, —C(O)O—, —CH=N—, —CH(OH)—, —NHC(O)NH—, —C(=NH)—; or (b) converting a compound of formula Ia into a compound of formula Ib

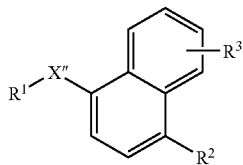
(Ib)

wherein $R^1$, $R^2$ and $R^3$ are as defined as in claim 1, and X″ is —SO—, —S(O)$_2$-(obtainable via process (b) when binding partner at $R^1$=C), —N(CH$_3$)—, —P(O)OH—, —CH$_2$NH—, —CH=CH—, and recovering the so obtained compound of formula Ia and formula Ib in free form or in form of a salt.

4. A pharmaceutical composition comprising a compound of claim 1 in free base or pharmaceutically acceptable acid salt form, in association with a pharmaceutical carrier or diluent.

\* \* \* \* \*